United States Patent
Ando et al.

(10) Patent No.: US 12,385,008 B2
(45) Date of Patent: Aug. 12, 2025

(54) METHOD FOR PRODUCING RETINAL TISSUE

(71) Applicants: SUMITOMO PHARMA CO., LTD., Osaka (JP); RIKEN, Wako (JP)

(72) Inventors: Satoshi Ando, Kobe (JP); Takao Kuroda, Kobe (JP); Yoshiki Sasai, Kobe (JP)

(73) Assignees: SUMITOMO PHARMA CO., LTD., Osaka (JP); RIKEN, Wako (JP)

( * ) Notice: Subject to any disclaimer, the term of this patent is extended or adjusted under 35 U.S.C. 154(b) by 0 days.

(21) Appl. No.: 15/758,255

(22) PCT Filed: Sep. 8, 2016

(86) PCT No.: PCT/JP2016/076523
§ 371 (c)(1),
(2) Date: Mar. 7, 2018

(87) PCT Pub. No.: WO2017/043604
PCT Pub. Date: Mar. 16, 2017

(65) Prior Publication Data
US 2018/0245039 A1    Aug. 30, 2018

(30) Foreign Application Priority Data

Sep. 8, 2015  (JP) .................................. 2015-176897

(51) Int. Cl.
*C12N 5/079*  (2010.01)
*A61K 35/30*  (2015.01)
(Continued)

(52) U.S. Cl.
CPC ............ *C12N 5/0621* (2013.01); *A61K 35/30* (2013.01); *C12N 5/10* (2013.01); *C12Q 1/02* (2013.01);
(Continued)

(58) Field of Classification Search
CPC .... A61K 35/545; A61K 35/30; C12N 5/0621; C12N 5/10; C12N 2500/90;
(Continued)

(56) References Cited

U.S. PATENT DOCUMENTS 6,030,794 A    2/2000 Chambon et al.
8,193,235 B2 *  6/2012 Paul ..................... C12N 5/0606
                                                        514/408
(Continued)

FOREIGN PATENT DOCUMENTS

CA    2937129 A1    7/2015
EP    1598417 A1    11/2005
(Continued)

OTHER PUBLICATIONS

Du et al. "Regulation of Retinal Progenitor Cell Differentiation by Bone Morphogenetic Protein 4 is Mediated by the Smad/Id Cascade" Investigative Ophthalmology & Visual Science, Jul. 2010, vol. 51, No. 7 (Year: 2010).*
(Continued)

*Primary Examiner* — Tracy Vivlemore
*Assistant Examiner* — Lauren K Van Buren
(74) *Attorney, Agent, or Firm* — Leydig, Voit & Mayer, Ltd.

(57) ABSTRACT

The present invention provides a production method of a retinal cell or retinal tissue, including the following steps:
(1) a first step of culturing mammalian pluripotent stem cells in the absence of a feeder cell for a period not exceeding 30 days in a medium comprising 1) a factor for maintaining an undifferentiated state and 2) an MEK inhibitor,
(2) a second step of culturing the cells obtained in the first step in suspension to form a cell aggregate, and
(3) a third step of culturing the aggregate obtained in the second step in suspension in the presence of a BMP signal
(Continued)

transduction pathway activating substance to obtain an aggregate containing retinal cells or a retinal tissue.

24 Claims, 3 Drawing Sheets

(51) Int. Cl.
*C12N 5/10* (2006.01)
*C12Q 1/02* (2006.01)
*G01N 33/50* (2006.01)
*A61K 35/545* (2015.01)

(52) U.S. Cl.
CPC ..... *G01N 33/5014* (2013.01); *G01N 33/5058* (2013.01); *A61K 35/545* (2013.01); *C12N 2500/90* (2013.01); *C12N 2501/115* (2013.01); *C12N 2501/155* (2013.01); *C12N 2501/41* (2013.01); *C12N 2501/727* (2013.01); *C12N 2506/45* (2013.01); *C12N 2513/00* (2013.01)

(58) Field of Classification Search
CPC ........ C12N 2501/115; C12N 2501/155; C12N 2501/41; C12N 2501/727; C12N 2506/45; C12N 2513/00; C12N 5/0696; C12Q 1/02; G01N 33/5014; G01N 33/5058
See application file for complete search history.

(56) References Cited

U.S. PATENT DOCUMENTS

| | | | |
|---|---|---|---|
| 8,372,642 | B2 | 2/2013 | Rajesh et al. |
| 10,100,282 | B2 | 10/2018 | Rajesh et al. |
| 2005/0232916 | A1 | 10/2005 | Martin et al. |
| 2006/0122111 | A1 | 6/2006 | Furukawa |
| 2008/0044901 | A1* | 2/2008 | Sasai ............... C12N 5/0621 435/325 |
| 2009/0053809 | A1 | 2/2009 | Zander et al. |
| 2010/0009442 | A1 | 1/2010 | Sasai et al. |
| 2010/0041137 | A1* | 2/2010 | Smith ............... C12N 5/0606 435/354 |
| 2010/0279403 | A1 | 11/2010 | Rajesh et al. |
| 2011/0091869 | A1 | 4/2011 | Sasai et al. |
| 2011/0274662 | A1 | 11/2011 | Malcuit et al. |
| 2012/0129211 | A1 | 5/2012 | Kattman et al. |
| 2012/0149598 | A1 | 6/2012 | Inoue et al. |
| 2012/0225480 | A1* | 9/2012 | Amit ............... C12N 5/0696 435/405 |
| 2013/0040330 | A1 | 2/2013 | Sasai et al. |
| 2013/0210141 | A1 | 8/2013 | Rajesh et al. |
| 2014/0017790 | A1* | 1/2014 | Suzuki ............... C12N 5/0696 435/377 |
| 2014/0220681 | A1* | 8/2014 | Valamehr ............ C12N 5/0607 435/377 |
| 2014/0308743 | A1 | 10/2014 | Sasai et al. |
| 2014/0341864 | A1* | 11/2014 | Nakano ............... A61L 27/3895 435/363 |
| 2015/0132787 | A1 | 5/2015 | Sasai et al. |
| 2016/0186134 | A1 | 6/2016 | Keller et al. |
| 2016/0186136 | A1 | 6/2016 | Sasai et al. |
| 2016/0251616 | A1 | 9/2016 | Nakano et al. |
| 2016/0264936 | A1* | 9/2016 | Nakano ............... A61P 27/00 |
| 2016/0376554 | A1 | 12/2016 | Kuwahara et al. |
| 2017/0198260 | A1 | 7/2017 | Miyajima et al. |
| 2017/0253853 | A1 | 9/2017 | Sasai et al. |
| 2017/0313976 | A1 | 11/2017 | Kuwahara et al. |
| 2017/0313981 | A1 | 11/2017 | Kuwahara et al. |

FOREIGN PATENT DOCUMENTS

| | | |
|---|---|---|
| EP | 1616941 A1 | 1/2006 |
| JP | 2012-519005 A | 8/2012 |
| JP | 2012-245007 A | 12/2012 |
| JP | 2013-099345 A | 5/2013 |
| WO | WO 2006/053629 A1 | 5/2006 |
| WO | WO 2008/129554 A1 | 10/2008 |
| WO | WO 2009/148170 A1 | 12/2009 |
| WO | WO 2011/043591 A2 | 4/2011 |
| WO | WO 2011/055855 A1 | 5/2011 |
| WO | WO 2012/073238 A1 | 6/2012 |
| WO | WO 2012/135621 A2 | 10/2012 |
| WO | WO 2013/065763 A1 | 5/2013 |
| WO | WO-2013077425 A1 * | 5/2013 ............. A61K 35/30 |
| WO | WO 2013/086236 A2 | 6/2013 |
| WO | WO 2014/121077 A2 | 8/2014 |
| WO | WO-2015025967 A1 * | 2/2015 ......... A61L 27/3834 |
| WO | WO-2015068505 A1 * | 5/2015 ............. A61K 35/30 |
| WO | WO-2015107738 A1 * | 7/2015 ........... C12N 5/0621 |
| WO | WO 2015/178498 A1 | 11/2015 |
| WO | WO 2016/039317 A1 | 3/2016 |
| WO | WO 2016/063985 A1 | 4/2016 |
| WO | WO 2016/063986 A1 | 4/2016 |

OTHER PUBLICATIONS

Theunissen et al. "Systematic Identification of Culture Conditions for Induction and Maintenance of Naive Human Pluripotency" Cell Stem Cell 15, 471-487, Oct. 2, 2014 (Electronic Publication Availability Date Jul. 24, 2014). (Year: 2014).*

Kuwahara et al. "Generation of a ciliary margin-like stem cell niche from self-organizing human retinal tissue" Nature Communications, ublished Feb. 19, 2015 (Year: 2015).*

Lee "Inhibition of pluripotnet stem cell-derived teratoma formation by small molecules" PNAS Aug. 5, 2013.*

Theunissen "Systematic Identification of Culture Conditions for Induction and Maintenance of Naive Human Pluripotency" Cell Stem Cell Oct. 2, 2014: 15(4) 471-487 (Year: 2014).*

Kuwahara et al. "Generation of ciliary-margin like stem cells niche from self-organizing human retinal tissue" Nature Communications (Year: 2015).*

Theunissen et al. "Systematic Identification of Culture Conditions for Induction and Maintenance of Naive Human Pluripotency" Cell Stem Cell 15, 471-487, Oct. 2, 2014. (Year: 2014).*

Du et al. "Regulation of Retinal Progenitor Cell Differentiation by Bone Morphogenetic Protein 4 is Mediated by the Smad/Id Cascade" Investigative Ophthalmology and Visual Science, Jul. 2010, vol. 51, No. 7. (Year: 2010).*

Merriam Webster Dictionary "cystic" (Year: 2024).*

Wikipedia Term Cyst (Year: 2024).*

Akopian et al. (The International Stem Cell Initiative Consortium), "Comparison of defined culture systems for feeder cell free propagation of human embryonic stem cells," *In Vitro Cell Dev. Biol. Anim.*, 46(3-4): 247-258 (2010).

Bhatia et al., "Distribution of Müller stem cells within the neural retina: Evidence for the existence of a ciliary margin-like zone in the adult human eye," *Exp. Eye Res.*, 89(3): 373-382 (2009).

Bhatia et al., "Adult Retinal Cells Revisited," *Open Ophthalmol. J.*, 4: 30-38 (2010).

Boucherie et al., "Brief Report: Self-Organizing Neuroepithelium from Human Pluripotent Stem Cells Facilitates Derivation of Photoreceptors," *Stem Cells*, 31(2): 408-414 (2013).

Chambers et al., "Highly efficient neural conversion of human ES and iPS cells by dual inhibition of SMAD signaling," *Nat. Biotechnol.*, 27(3): 275-280 and Corrigendum (2009).

Chen et al., "Chemically defined conditions for human iPSC derivation and culture," *Nat. Methods*, 8(5): 424-429 and Supplemental Online Methods (2011).

Denayer et al., "Canonical Wnt signaling Controls Proliferation of Retinal Stem/Progenitor Cells in Postembryonic *Xenopus* Eyes," *Stem Cells*, 26(8): 2063-2074 (2008).

Doi et al., "Isolation of Human Induced Pluripotent Stem Cell-Derived Dopaminergic Progenitors by Cell Sorting for Successful Transplantation," *Stem Cell Reports*, 2(3): 337-350 (2014).

Eiraku et al., "Self-Organized Formation of Polarized Cortical Tissues from ESCs and Its Active Manipulation by Extrinsic Signals," *Cell Stem Cell*, 3(5): 519-532 (2008).

(56) References Cited

OTHER PUBLICATIONS

Eiraku et al., "Self-organizing optic-cup morphogenesis in three-dimensional culture," *Nature*, 472(7341): 51-56 (2011).
Eiraku et al., "Relaxation-expansion model for self-driven retinal morphogenesis: A hypothesis from the perspective of biosystems dynamics at the multi-cellular level," *Bioessays*, 34(1): 17-25 (2012).
Fischer et al., "The ciliary marginal zone (CMZ) in development and regeneration of the vertebrate eye," *Exp. Eye Res.*, 116: 199-204 (2013).
Fuhrmann, "Wnt signaling in eye organogenesis," *Organogenesis*, 4(2): 60-67 (2008).
Furuta et al., "BMP4 is essential for lens induction in the mouse embryo," *Genes Dev.*, 12(23): 3764-3775 (1998).
Greber et al., "FGF signaling inhibits neural induction in human embryonic stem cells," *Embo J.*, 30(24): 4874-4884 (2011).
Hedge et al., "Expression of Shisa2, a modulator of both Wnt and Fgf signaling, in the chick embryo," *Int. J. Dev. Biol.*, 52(1): 81-85 (2008).
Hirami et al., "Generation of retinal cells from mouse and human induced pluripotent stem cells," *Neurosci. Lett.*, 458(3): 126-131 (2009).
Ikeda et al., "Generation of Rx$^+$ / Pax6$^+$ neural retinal precursors from embryonic stem cells," *Proc. Natl. Acad. Sci. USA*, 102(32): 11331-11336 (2005).
Ikeda et al., "In vitro neuronal differentiation induction using ES cells —telencephalic precursors and neural retinal precursors," *Experimental Medicine*, 24(2): 188-194 and Additional Figures (2006).
Inoue et al., "Activation of Canonical Wnt Pathway Promotes Proliferation of Retinal Stem Cells Derived from Adult Moose Ciliary Margin," *Stem Cells*, 24(1): 95-104 (2006).
Jaeger et al., "Temporally controlled modulation of FGF/ERK signaling directs midbrain dopaminergic neural progenitor fate in mouse and human pluripotent stem cells," *Development*, 138(20): 4363-4374 (2011).
Kadoshima et al., "Self-organization of axial polarity, inside-out layer pattern, and species-specific progenitor dynamics in human ES cell-derived neocortex," *Proc. Natl. Acad. Sci. USA*, 110(50): 20284-20289 (2013).
Kubo et al., "Wnt2b controls retinal cell differentiation at the ciliary marginal zone," *Development*, 130(3): 587-598 (2003).
Kubo et al., "Hairy1 acts as a node downstream of Wnt Signaling to maintain retinal stem cell-like progenitor cells in the chick ciliary marginal zone," *Development*, 136(11): 1823-1833 (2009).
Kuwahara et al., "Generation of a ciliary margin-like stem cell niche from self-organizing human retinal tissue," *Nat. Commun.*, 6: 6286 (2015).
Lamba et al., "Efficient generation of retinal progenitor cells from human embryonic stem cells," *Proc. Natl. Acad. Sci. USA*, 103(34): 12769-12774 (2006).
Lancaster et al., "Cerebral organoids model human brain development and microcephaly," *Nature*, 501(7467): 373-379 (2013).
Lang, "Pathways regulating lens induction in the mouse," *Int. J. Dev. Biol.*, 48(8-9): 783-791 (2004).
La Torre et al., "Production and Transplantation of Retinal Cells from Human and Mouse Embryonic Stem Cells," *Methods Mol. Biol.*, 884: 229-246 (2012).
Liu et al., "Ciliary margin transdifferentiation from neural retina is controlled by canonical Wnt signaling," *Dev. Biol.*, 308(1): 54-67 (2007).
Morizane et al., "Neural Induction with a Dopaminergic Phenotype from Human Pluripotent Stem Cells Through a Feeder-Free Floating Aggregation Culture," *Methods Mol. Biol.*, 1018: 11-19 (2013).
Moshiri et al., "Sonic Hedgehog Regulates Proliferation of the Retinal Ciliary Marginal Zone in Posthatch Chicks," *Dev. Dyn.*, 233(1): 66-75 (2005).
Muguruma et al., "Ontogeny-recapitulating generation and tissue integration of ES cell-derived Purkinje cells," *Nat. Neurosci.*, 13(10): 1171-1180 and Supplemental Online Methods (2010).
Nakagawa et al., "A novel efficient feeder-free culture system for the derivation of human induced pluripotent stem cells," *Sci. Rep.*, 4: 3594 (2014).
Nakano et al., "Self-Formation of Optic Cups and Storable Stratified Neural Retina from Human ESCs," *Cell Stem Cell*, 10(6): 771-785 (2012).
Osakada et al., "Control of neural differentiation from pluripotent stem cells," *Inflammation and Regeneration*, 28(3): 166-173 (2008).
Osakada et al., "Toward the generation of rod and cone photoreceptors from mouse, monkey and human embryonic stem cells," *Nat. Biotechnol.*, 26(2): 215-224 (2008).
Osakada et al., "In vitro differentiation of retinal cells from human pluripotent stem cells by small-molecule induction," *J. Cell Sci.*, 122(17): 3169-3179 (2009).
Osakada et al., "Neural Induction and Patterning in Mammalian Pluripotent Stem Cells," *CNS Neurol. Disord. Drug Targets*, 10: 419-432 (2011).
Ozair et al., "Neural induction and early patterning in vertebrates," *WIREs Dev. Biol.*, 2(4): 479-498 (2013).
Phillips et al., "Blood-Derived Human iPS Cells Generate Optic Vesicle-Like Structures with the Capacity to Form Retinal Laminae and Develop Synapses," *Invest. Ophthalmol. Vis. Sci.*, 53(4): 2007-2019 (2012).
Sasai et al., "Self-organization as seen in pattern formation of neural tissue: Challenge to Emergent Biology," *Brain Science Review*, 99-112 (2014).
Seiler et al., "Visual restoration and transplant connectivity in degenerate rats implanted with retinal progenitor cells," *Eur. J. Neurosci.*, 31(3): 508-520 (2010).
Spence et al., "The hedgehog pathway is a modulator of retina regeneration," *Development*, 131(18): 4607-4621 (2004).
Stephens et al., "Loss of adenomatous polyposis coli (apc) Results in an Expanded Ciliary Marginal Zone in the Zebrafish Eye," *Dev. Dyn.*, 239(7): 2066- 2077 (2010).
Suga et al., "Self-formation of functional adeno-hypophysis in three-dimensional culture," *Nature*, 480(7375): 57-62 and Supplemental Methods (2011).
Susaki et al., "MEK mediates in vitro neural transdifferentiation of the adult newt retinal pigment epithelium cells: Is FGF2 an induction factor?" *Pigment Cell Res.*, 20(5): 364-379 (2007).
Trousse et al., "BMP4 Mediates Apoptotic Cell Death in the Developing Chick Eye," *J. Neurosci.*, 21(4): 1292-1301 (2001).
Vugler et al., "Embryonic stem cells and retinal repair," *Mech. Dev.*, 124(11-12): 807-829 (2007).
Watanabe et al., "Directed differentiation of telencephalic precursors from embryonic stem cells," *Nat. Neurosci.*, 8(3): 288-296 (2005).
Wei et al., "Isolation and Identification of retinal stem cells in mouse eye," *Journal of Third Military Medical University*, 25(24): 2161-2164 (2003).
Yang et al., "Efficient generation of lens progenitor cells and lentoid bodies from human embryonic stem cells in chemically defined conditions," *FASEB J.*, 24(9): 3274-3283 (2010).
Yang et al., "Directed Differentiation into Neural Lineages and Therapeutic Potential of Porcine Embryonic Stem Cells in Rat Parkinson's Disease Model," *Cell. Repogram.*, 12(4): 447-461 (2010).
Chinese Patent Office, The First Office Action in Chinese Patent Application No. 201380041868.X (Jan. 15, 2016).
European Patent Office, Extended European Search Report in European Patent Application No. 14838289.8 (Apr. 4, 2017).
European Patent Office, Extended European Search Report in European Patent Application No. 14869571.1 (Jun. 7, 2017).
Japanese Patent Office, International Search Report in International Patent Application No. PCT/JP2013/065878 (Jul. 30, 2013).
Japanese Patent Office, International Preliminary Report on Patentability in International Patent Application No. PCT/JP2013/065878 (Dec. 9, 2014).
Japanese Patent Office, International Search Report in International Patent Application No. PCT/JP2014/072065 (Nov. 25, 2014).
Japanese Patent Office, Written Opinion of the International Searching Authority in International Patent Application No. PCT/JP2014/072065 (Nov. 25, 2014).

(56) References Cited

OTHER PUBLICATIONS

Japanese Patent Office, International Search Report in International Patent Application No. PCT/JP2016/076523 (Dec. 13, 2016).
Intellectual Property Office of Singapore, Search Report in Singaporean Patent Application No. 11201601294P (Feb. 22, 2017).
Intellectual Property Office of Singapore, Search Report in Singaporean Patent Application No. 11201604705U (May 5, 2017).
Chuang et al., "Neural differentiation from embryonic stem cells in vitro: An overview of the signaling pathways," *World J. Stem Cells*, 7(2): 437-447 (2015).
Croze et al., "Differentiation of Pluripotent Stem Cells into Retinal Pigmented Epithelium," *Dev. Ophthalmol.*, 53: 81-96 (2014).
Meyer et al., "Modeling early retinal development with human embryonic and induced pluripotent stem cells," *Proc. Natl. Acad. Sci. U.S.A.*, 106(39): 16698-16703 (2009).
European Patent Office, Extended European Search Report in European Patent Application No. 16844465.1 (Jan. 31, 2019).
Hiraki et al., "Culturing Human IPS Cells Under Non-feeder Conditions Alters Their Basic Pluripotent Status," *Joint Conference of the 33rd Annual Meeting of the Molecular Biology Society of Japan and 83rd Annual Meeting of the Japanese Biochemical Society*, Abstract No. 4P-0894 (2010).
Ying et al., "The Ground State of Embryonic Stem Cell Self-Renewal," *Nature*, 453(7194): 519-523 and Supplementary Information (2008).
Bardot et al.,"Mouse gastrulation: Coordination of tissue patterning, specification and diversification of cell fate," *Mechanisms of Development*, 163 10617 (2020).
Sumi et al., "Defining early lineage specification of human embryonic stem cells by the orchestrated balance of canonical Wnt/β-catenin, Activin/Nodal and BMP signaling," *Development*, 135(17): 2969-2979 (2008).
Desai et al., "Human embryonic stem cell cultivation: historical perspective and evolution of xeno-free culture systems," *Reprod. Biol. and Endocrinol.*, 13: 9 (2015).
Kuwahara et al., "Preconditioning the Initial State of Feeder-free Human Pluriopotent Stem Cells Promotes Self-formation of Three-dimensional Retinal Tissue," *Sci. Rep.*, 9(1): 18936 (2019).
Toivonen et al., "Comparative Analysis of Targeted Differentiation of Human Induced Pluripotent Stem Cells (hiPSCs) and Human Embryonic Stem Cells Reveals Variability Associated With Incomplete Transgene Silencing in Retrovirally Derived hiPSC Lines," *Stem Cells Transl. Med.*, 2(2): 83-93 (2013).

\* cited by examiner

METHOD FOR PRODUCING RETINAL TISSUE

CROSS-REFERENCE TO RELATED APPLICATIONS

This patent application is the U.S. national phase of International Patent Application No. PCT/JP2016/076523, filed Sep. 8, 2016, which claims the benefit of Japanese Patent Application No. 2015-176897, filed on Sep. 8, 2015, which are incorporated by reference in their entireties herein.

TECHNICAL FIELD

The present invention relates to a method for producing retinal cells or a retinal tissue from pluripotent stem cells.

BACKGROUND ART

As a method for producing a neural tissue such as retinal tissue from pluripotent stem cells, a method for producing neural tissue which comprises forming uniformed aggregates of pluripotent stem cells in a serum-free medium, culturing them in suspension, culturing them in suspension in a medium for differentiation induction in the presence of a differentiation-inducing factor and the like as appropriate to induce differentiation of pluripotent stem cells into the intended neural cells has been reported (patent document 1 and non-patent document 1). For example, a method for obtaining a multi-layered retinal tissue from pluripotent stem cells (patent document 2 and non-patent document 2), and a method for obtaining multi-layered retinal tissue which comprises forming uniformed aggregates of pluripotent stem cells in a serum-free medium containing a Wnt signal pathway inhibitor, followed by culturing them in suspension in the presence of a basement membrane preparation, and then culturing them in suspension in a serum-containing medium (patent document 3 and non-patent document 3) are known. In addition, a method for inducing differentiation of pluripotent stem cells into a hypothalamic tissue (patent document 4 and non-patent document 4), and a method inducing differentiation of pluripotent stem cells into neural progenitor cells (non-patent documents 5 and 6) have also been reported. A method for producing a retina related cell or a retinal tissue, comprising culturing aggregates of pluripotent stem cells in suspension in a medium not containing a Sonic hedgehog signal transduction pathway activating substance but containing a BMP signal transduction pathway activating substance has been reported (patent document 5 and non-patent document 10).

The pluripotent stem cells as a starting material of these production methods, particularly in the case of primate pluripotent stem cells, were cultured in the presence of feeder cells under conditions for maintaining an undifferentiated state by adding a factor(s) for maintaining an undifferentiated state (undifferentiated maintenance culture method). In recent years, improvement has been made in the culturing method for maintaining an undifferentiated state, and a method of culturing primate pluripotent stem cells in the absence of a feeder cell (under feeder-free conditions) with the addition of a factor for maintaining an undifferentiated state has been reported (non-patent document 7, non-patent document 8 and non-patent document 9).

DOCUMENT LIST

Patent Documents patent document 1: WO 2009/148170
patent document 2: WO 2011/055855
patent document 3: WO 2013/077425
patent document 4: WO 2013/065763
patent document 5: WO 2015/025967

Non-Patent Document non-patent document 1: Cell Stem Cell, 3, 519-32 (2008)
non-patent document 2: Nature, 472, 51-56 (2011)
non-patent document 3: Cell Stem Cell, 10(6), 771-775 (2012)
non-patent document 4: Nature, 480, 57-62 (2011)
non-patent document 5: Nature Biotechnology, 27(3), 275-80 (2009)
non-patent document 6: Proc Natl Acad Sci USA, 110(50), 20284-9 (2013)
non-patent document 7: Nature Methods, 8, 424-429 (2011)
non-patent document 8: Scientific Reports, 4, 3594 (2014)
non-patent document 9: In Vitro Cell Dev Biol Anim., 46, 247-58 (2010)
non-patent document 10: Nature Communications, 6 (2015), Article number: 6286

SUMMARY OF THE INVENTION

Problems to be Solved by the Invention

The problem to be solved by the present invention is provision of a method for efficiently producing retinal cells or retinal tissues from pluripotent stem cells prepared or maintenance cultured in the absence of a feeder cell (under feeder-free conditions).

Means of Solving the Problems

The present inventors have conducted studies in an attempt to solve the aforementioned problems and found that a cell aggregate containing retinal cells can be formed with high efficiency by culturing pluripotent stem cells in the absence of a feeder cell (under feeder-free conditions) in a medium containing (1) a factor for maintaining an undifferentiated state and (2) a MAP kinase kinase inhibitor (MEK inhibitor), and then culturing the cells in suspension.

In addition, they have found that a cell aggregate containing retinal cells can be formed with high efficiency by culturing pluripotent stem cells in the absence of a feeder cell (under feeder-free conditions) in a medium containing (1) a factor for maintaining an undifferentiated state, (2) a MAP kinase kinase inhibitor (MEK inhibitor) and (3) a PKC inhibitor or a B-Raf inhibitor, and then culturing the cells in suspension. Moreover, they have found that by using this cell aggregate, retinal cells and retinal tissues can be induced with high efficiency, which resulted in the completion of the present invention.

That is, the present invention relates to the following.

[1] A method for producing a retinal cell or a retinal tissue, comprising the following steps:
(1) a first step of culturing a mammalian pluripotent stem cell in the absence of a feeder cell for a period not exceeding 30 days in a medium comprising 1) a factor for maintaining an undifferentiated state and 2) an MEK inhibitor, (2) a second step of culturing the cell obtained in the first step in suspension to form a cell aggregate, and (3) a third step of culturing the aggregate obtained in the second step in suspension in the presence of a BMP signal transduction pathway activating substance to obtain an aggregate containing a retinal cell or a retinal tissue.

[2] The production method according to [1], wherein the medium in the first step further comprises a PKC inhibitor or a B-Raf inhibitor.

[3] The production method according to [1] or [2], wherein the first step is performed under serum-free conditions.

[4] The production method according to any of [1] to [3], wherein the culture period is 0.5 day-8 days in the first step.

[5] The production method according to [4], wherein the culture period is 1 day-6 days in the first step.

[6] The production method according to [5], wherein the culture period is 4 days-6 days in the first step.

[7] The production method according to any of [1] to [6], wherein the first step is performed with an adhesion culture method.

[8] The production method according to any of [1] to [7], wherein the factor for maintaining an undifferentiated state is an FGF signal transduction pathway activating substance.

[9] The production method according to [8], wherein the FGF signal transduction pathway activating substance is bFGF.

[10] The production method according to any of [1] to [9], wherein the MEK inhibitor is PD0325901.

[11] The production method according to any of [2] to [10], wherein the PKC inhibitor is Go6983.

[12] The production method according to any of [2] to [11], wherein the B-Raf inhibitor is SB590885.

[13] The production method according to any of [1] to [12], wherein the cells are cultured in the presence of a ROCK inhibitor in the first step.

[14] The production method according to [13], wherein the ROCK inhibitor is Y-27632.

[15] The production method according to any of [1] to [14], wherein the cells are cultured in suspension in a serum-free medium containing a Sonic hedgehog signal transduction pathway activating substance in the second step.

[16] The production method according to [15], wherein the Sonic hedgehog signal transduction pathway activating substance is SAG.

[17] The production method according to any of [1] to [16], wherein the BMP signal transduction pathway activating substance is one or more proteins selected from the group consisting of BMP2, BMP4, BMP7 and GDF7.

[18] The production method according to [17], wherein the BMP signal transduction pathway activating substance is BMP4.

[19] The production method according to any of [1] to [18], wherein, in the second step, the concentration of the Sonic hedgehog signal transduction pathway activating substance in the medium is a concentration corresponding to Sonic hedgehog signal transduction activity of SAG at 10 nM to 700 nM.

[20] The production method according to any of [1] to [19], wherein, in the third step, the BMP signal transduction pathway activating substance is added to the medium at a point between day 1 and day 9 from the start of the second step.

[21] The production method according to [20], wherein, in the third step, the BMP signal transduction pathway activating substance is added to the medium at a point between day 3 and day 6 from the start of the second step.

[22] The production method according to any of [1] to [21], wherein uniformed aggregates are formed in the second step.

[23] The production method according to any of [1] to [22], wherein the suspension culturing is performed in the absence of a basement membrane preparation.

[24] The production method according to any of [1] to [23], wherein the pluripotent stem cell is an induced pluripotent stem cell.

[25] The production method according to [24], wherein the induced pluripotent stem cell is a human induced pluripotent stem cell.

[26] A method for treating a disease due to a disorder of a retinal cell or retinal tissue, comprising transplanting an effective amount of retinal cells or a retinal tissue produced by the method according to any of [1] to [25] to a subject in need of the transplantation.

[27] A retinal cell or retinal tissue produced by the method according to any of [1] to [25] for use in the treatment of a disease due to a disorder of a retinal cell or retinal tissue.

[28] A pharmaceutical composition comprising a retinal cell or retinal tissue produced by the method according to any of [1] to [25] as an active ingredient.

[29] The pharmaceutical composition according to [28], wherein the retinal cell is a retinal progenitor cell and/or a retinal layer specific nerve cell.

[30] A method for evaluating toxicity or efficacy of a test substance, comprising bringing a retinal cell or a retinal tissue produced by the method according to any of [1] to [25] into contact with the substance, and assaying the effect of the substance on the cell or tissue.

Effect of the Invention

According to the present invention, a cell aggregate capable of differentiating into a retinal cell, and a retinal cell and a retinal tissue can be produced with high efficiency from pluripotent stem cells cultured in the absence of a feeder cell.

DESCRIPTION OF EMBODIMENTS

1. Definition

Figure 1:
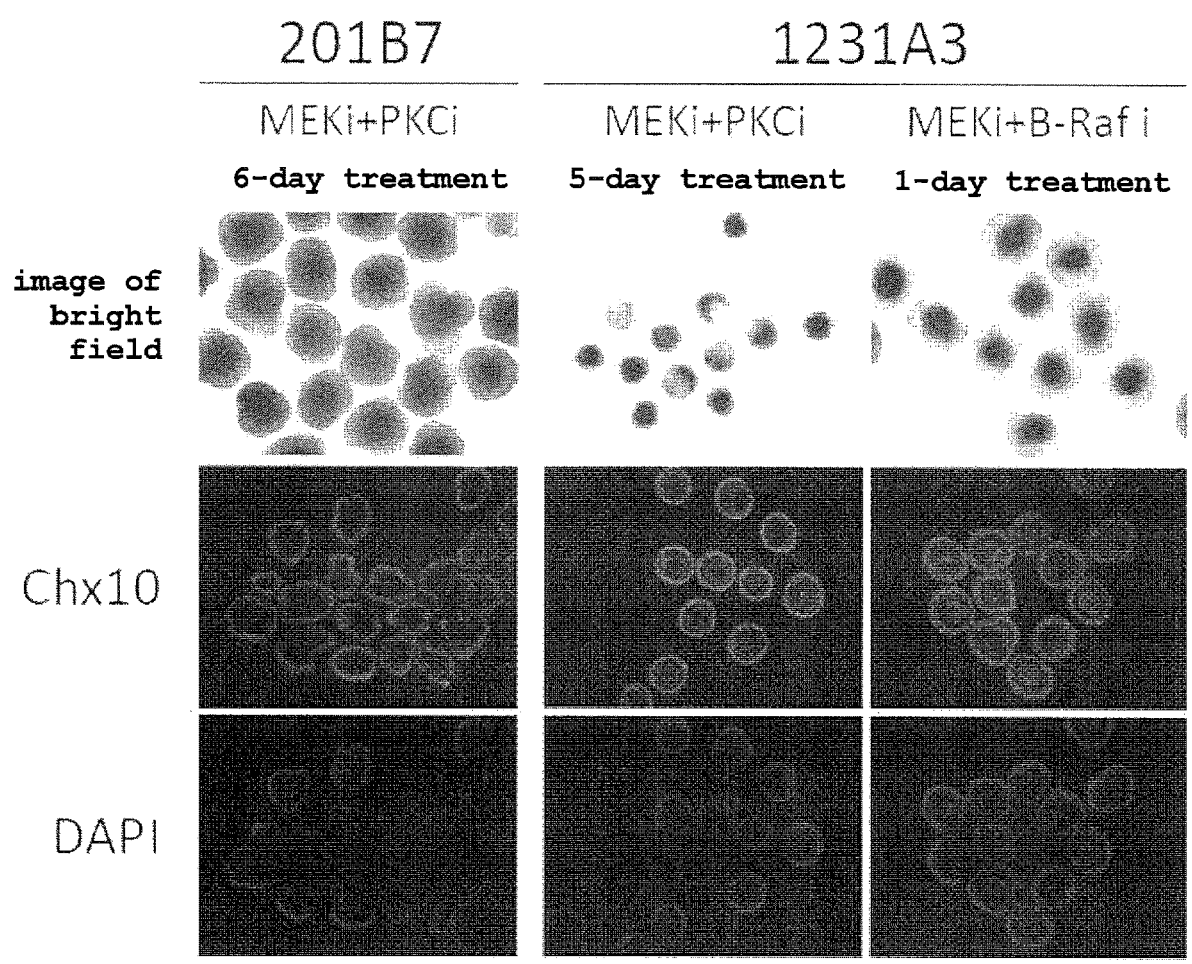
FIG. 1 shows microscopic images of cell aggregates containing retinal progenitor cells derived from human iPS cells produced by a production method of a retinal tissue comprising a step of culturing the human iPS cells in a medium containing an MEK inhibitor, and a PKC inhibitor or a B-Raf inhibitor. 201B7: human iPS cells (201B7 strain) were used. On day 20 after suspension culture. 1231A3: human iPS cells (1231A3 strain) were used. On day 21 after suspension culture. Chx10: retinal progenitor cell marker. DAPI: cell nuclear staining. MEKi: MEK inhibitor (1 μM PD0325901), PKCi: PKC inhibitor (2 μM Go6983), B-Raf is B-Raf inhibitor (0.5 μM SB590885).

In the present invention, "stem cell" means an undifferentiated cell having differentiation potency and proliferative capacity (particularly self-renewal competence) maintaining differentiation potency. The stem cell includes subpopulations such as pluripotent stem cell, multipotent stem cell, unipotent stem cell and the like according to the differentiation potency. Pluripotent stem cell refers to a stem cell capable of being cultured in vitro and having a potency to differentiate into any cell lineage belonging to three germ layers (ectoderm, mesoderm, endoderm) (pluripotency). The multipotent stem cell means a stem cell having a potency to differentiate into plural types of tissues or cells, though not all kinds. The unipotent stem cell means a stem cell having a potency to differentiate into a particular tissue or cell.

Pluripotent stem cell can be induced from fertilized egg, clone embryo, germ stem cell, stem cell in a tissue, and the like. Examples of the pluripotent stem cell include embryonic stem cell (ES cell), EG cell (embryonic germ cell), induced pluripotent stem cell (iPS cell) and the like.

Embryonic stem cell was first established in 1981, and has also been applied to the generation of knockout mouse since 1989. In 1998, human embryonic stem cell was established, which is also being utilized for regenerative medicine. ES cell can be produced by culturing an inner cell mass on a feeder cell or in a medium containing LIF. The production methods of ES cell are described in, for example, WO 96/22362, WO 02/101057, U.S. Pat. No. 5,843,780, U.S. Pat. No. 6,200,806, U.S. Pat. No. 6,280,718 and the like. Embryonic stem cells are available from given organizations, or a commercially available product can be purchased. For example, human embryonic stem cells, KhES-1, KhES-2 and KhES-3, are available from Kyoto University's Institute for Frontier Medical Sciences. EB5 cell, which is a mouse embryonic stem cell, is available from Incorporated Administrative Agency RIKEN, and D3 cell line, which is a mouse embryonic stem cell, is available from ATCC.

Nuclear transfer ES cell (ntES cell), which is one of the ES cells, can be established from a clone embryo produced by transplanting the nucleus of a somatic cell into an egg from which a cell line is removed.

The "induced pluripotent stem cell" (also called iPS cell) in the present invention is a cell induced to have pluripotency by reprogramming a somatic cell by a known method and the like. Specifically, a cell induced to have pluripotency by reprogramming differentiated somatic cells such as fibroblast, peripheral blood mononuclear cell and the like by the expression of a combination of a plurality of genes selected from the group consisting of reprogramming genes including Oct3/4, Sox2, Klf4, Myc (c-Myc, N-Myc, L-Myc), Glis1, Nanog, Sal14, lin28, Esrrb and the like can be mentioned. Examples of preferable combination of reprogramming factors include (1) Oct3/4, Sox2, Klf4, and Myc (c-Myc or L-Myc), and (2) Oct3/4, Sox2, Klf4, Lin28 and L-Myc (Stem Cells, 2013; 31:458-466) and the like.

Induced pluripotent stem cell was established by Yamanaka et al. in mouse cell in 2006 (Cell, 2006, 126(4), pp. 663-676). In 2007, Induced pluripotent stem cell was also established from human fibroblast, and has pluripotency and self-renewal competence similar to those of embryonic stem cells (Cell, 2007, 131(5), pp. 861-872; Science, 2007, 318(5858), pp. 1917-1920; Nat. Biotechnol., 2008, 26(1), pp. 101-106). Various improvements have thereafter been made in the induction method of induced pluripotent stem cells (e.g., mouse iPS cell: Cell. 2006 Aug. 25; 126(4):663-76, human iPS cell: Cell. 2007 Nov. 30; 131(5):861-72).

Besides the production method of induced pluripotent stem cells based on direct reprogramming by gene expression, induced pluripotent stem cell can also be obtained from somatic cell by the addition of a compound and the like (Science, 2013, 341, pp. 651-654).

It is also possible to obtain established induced pluripotent stem cell and, for example, human induced pluripotent cell lines established by Kyoto University such as 201B7 cell, 201B7-Ff cell, 253G1 cell, 253G4 cell, 1201C1 cell, 1205D1 cell, 1210B2 cell, 1231A3 cell, Ff-I01 cell, QHJI01 cell and the like are available from the National University Corporation Kyoto University and iPS Academia Japan, Inc.

While the somatic cell used for obtaining induced pluripotent stem cell is not particularly limited, tissue-derived fibroblast, blood-lineage cells (e.g., peripheral blood mononuclear cell, T cell), hepatocyte, pancreatic cell, intestinal epithelial cell, smooth muscle cell and the like can be mentioned. As the fibroblast, those derived from dermis and the like can be mentioned.

When induced pluripotent stem cell is produced by reprogramming by the expression of several kinds of genes, the means for gene expression is not particularly limited. Examples of the aforementioned means include an infection method using a virus vector (e.g., retrovirus vector, lentivirus vector, Sendaivirus vector, adenovirus vector, adeno-associated virus vector), a gene transfer method using a plasmid vector (e.g., plasmid vector, episomal vector) (e.g., calcium phosphate method, lipofection method, RetroNectin method, electroporation method), a gene transfer method using an RNA vector (e.g., calcium phosphate method, lipofection method, electroporation method), a method with direct injection of protein and the like.

The pluripotent stem cell to be used in the present invention is preferably ES cell or induced pluripotent stem cell, more preferably induced pluripotent stem cell.

Genetically-modified pluripotent stem cells can be produced by using, for example, a homologous recombination technique. Examples of the gene on the chromosome to be modified include a cell marker gene, a histocompatibility antigen gene, a gene related to a disease due to a disorder of retinal cell and so on. A target gene on the chromosome can be modified using the methods described in Manipulating the Mouse Embryo, A Laboratory Manual, Second Edition, Cold Spring Harbor Laboratory Press (1994); Gene Targeting, A Practical Approach, IRL Press at Oxford University Press (1993); Biomanual Series 8, Gene Targeting, Making of Mutant Mouse using ES cell, YODOSHA CO., LTD. (1995); and so on.

To be specific, for example, the genomic DNA comprising the target gene to be modified (e.g., cell marker gene, histocompatibility antigen gene, disease-related gene and so on) is isolated, and a targeting vector used for homologous recombination of the target gene is produced using the isolated genomic DNA. The produced targeting vector is introduced into stem cells and the cells that showed homologous recombination between the target gene and the targeting vector are selected, whereby stem cells having the modified gene on the chromosome can be produced.

Examples of the method for isolating genomic DNA comprising the target gene include known methods described in Molecular Cloning, A Laboratory Manual, Second Edition, Cold Spring Harbor Laboratory Press (1989), Current Protocols in Molecular Biology, John Wiley & Sons (1987-1997) and so on. The genomic gene comprising the target gene can also be isolated using genomic DNA library screening system (manufactured by Genome Systems), Universal GenomeWalker Kits (manufactured by CLONTECH) and so on. A polynucleotide encoding the target protein can also be used instead of genome DNA. The polynucleotide can be obtained by amplifying the corresponding polynucleotide by the PCR method.

Production of targeting vector used for homologous recombination of the target gene, and efficient selection of a homologous recombinant can be performed according to the methods described in Gene Targeting, A Practical Approach, IRL Press at Oxford University Press (1993); Biomanual Series 8, Gene Targeting, Making of Mutant Mouse using ES cell, YODOSHA CO., LTD. (1995); and so on. As the targeting vector, any of replacement type or insertion type can be used. As the selection method, methods such as positive selection, promoter selection, negative selection, polyA selection and so on can be used.

Examples of a method for selecting the desired homologous recombinant from the selected cell lines include Southern hybridization method, PCR method and so on for the genomic DNA.

The "mammal" in the present invention encompasses rodents, ungulata, carnivora, primates and the like. The rodents encompass mouse, rat, hamster, guinea pig and the like. Ungulata encompass swine, bovine, goat, horse, sheep and the like. Carnivora encompasses dog, cat and the like. The "primates" in the present invention refers to mammals belonging to the primate, and the primates include strepsirhini such as lemur, loris, tupai and the like, and anthropoidea such as monkey, ape, human and the like.

The pluripotent stem cells to be used in the present invention are mammalian pluripotent stem cells, preferably pluripotent stem cells of rodents (e.g., mouse, rat) or primates (e.g., human, monkey), more preferably human pluripotent stem cells.

The pluripotent stem cell to be used in the present invention is most preferably human induced pluripotent stem cell (human iPS cell).

The "suspension culturing" or "suspension culture method" in the present invention refers to culturing while maintaining a state in which cells or cell aggregates are suspended in a culture medium and a method of performing the culture. That is, suspension culturing is performed under conditions in which cells or cell aggregates are not adhered to a culture vessel and the like, and culturing performed under conditions permitting adhesion to a culture vessel and the like (adhesion culturing or adhesion culture method) is not included in the category of suspension culturing. In this case, adhesion of cell means that a strong cell-substratum junction is formed between a cell or cell aggregate and a culture vessel. More particularly, suspension culturing refers to culturing under conditions in which a strong cell-substratum junction is not formed between a cell or cell aggregate and a culture vessel, and "adhesion culturing" refers to culturing under conditions in which a strong cell-substratum junction is formed between a cell or cell aggregate and a culture vessel and the like.

In a cell aggregate in suspension culture, a planar cell-cell adhesion is formed. In cell aggregates in suspension culture, a cell-substratum junction is hardly formed with a culture vessel and the like and, even if it is formed, its contribution is small. In some embodiment, an endogenous cell-substratum junction is present inside the aggregate, but a cell-substratum junction is hardly formed with a culture vessel and the like and, even if it is formed, its contribution is small.

The planar cell-cell adhesion (plane attachment) means that a cell attaches to another cell via planes. More particularly, the planar cell-cell adhesion means that, for example, not less than 1%, preferably not less than 3%, more preferably not less than 5%, of the surface area of a cell adheres to the surface of another cell. A surface of a cell can be observed by staining with a reagent (e.g., DiI) that stains membranes, immunostaining of cell adhesion molecules (e.g., E-cadherin and N-cadherin).

The cell culture vessel to be used when performing suspension culturing is not particularly limited as long as it enables "culturing in suspension" and those of ordinary skill in the art can appropriately determine same. Examples of such cell culture vessel include flask, tissue culture flask, dish, petri dish, tissue culture dish, multidish, microplate, microwell plate, micropore, multiplate, multiwell plate, chamber slide, schale, tube, tray, culture bag, spinner flask, roller bottle and so on. To enable suspension culturing, these culture vessels are preferably non-cell-adherent. Useful non-cell-adherent culture vessels include culture vessels whose surfaces have not undergone an artificial treatment for improving the cell adhesiveness (e.g., surface treatment such as coating treatment with extracellular matrix such as basement membrane preparation, laminin, entactin, collagen, gelatin etc., and the like, or polymer such as polylysine, polyornithine and the like or positive electric charge treatment and the like), and the like. As a non-cell-adherent culture vessel, culture vessels whose surfaces have been artificially treated to decrease adhesiveness to the cells (e.g., superhydrophilic treatment with MPC polymer and the like, protein low adsorption treatment etc.) and the like can be used. Roller culture using spinner flask, roller bottle and the like may be performed. The culture surface of the culture vessel may be a flat bottom or may have concaves and convexes.

As a culture vessel used for adhesion culturing, culture vessels whose surfaces have been artificially treated to improve cell adhesiveness (e.g. surface treatment such as coating treatment with extracellular matrix such as basement membrane preparation, laminin, entactin, collagen, gelatin, Matrigel, Synthemax, vitronectin and the like, or polymers such as polylysine, polyornithine and the like, or surface-processing by a positive electric charge treatment) and the like can be mentioned.

The medium to be used for culturing cells in the present invention can be prepared from a medium generally used for culturing animal cells as a basal medium. Examples of the basal medium include media that can be used for culturing animal cells such as BME medium, BGJb medium, CMRL1066 medium, Glasgow MEM medium, Improved MEM Zinc Option medium, IMDM medium, Medium199 medium, Eagle MEM medium, aMEM medium, DMEM medium, F-12 medium, DMEM/F-12 medium, IMDM/F12 medium, Ham medium, RPMI1640 medium, Fischer's medium, and mixed medium thereof etc.

The "serum-free medium" in the present invention means a medium free of unadjusted or unpurified serum. In the present invention, a medium containing purified blood-derived components and animal tissue-derived components (e.g., growth factor) is also included in a serum-free medium unless unadjusted or unpurified serum is contained therein.

The "serum-free conditions" means conditions free of unadjusted or unpurified serum, specifically, conditions using a serum-free medium.

The serum-free medium may contain a serum replacement. Examples of the serum replacement include one appropriately containing albumin, transferrin, fatty acid, collagen precursor, trace element, 2-mercaptoethanol or 3' thiolglycerol, or equivalents of these etc., and so on. Such serum replacement may be prepared by, for example, the method described in WO98/30679. The serum replacement may also be a commercially available product. Examples of such commercially available serum replacement include Knockout™ Serum Replacement (Life Technologies: hereinafter sometimes to be indicated as KSR), Chemically Defined Lipid Concentrated (manufactured by Life Technologies) and Glutamax™ (manufactured by Life Technologies), B27 (manufactured by Life Technologies), N2 (manufactured by Life Technologies).

The serum-free medium to be used for suspension culturing may appropriately contain a fatty acid or lipid, amino acid (e.g., non-essential amino acids), vitamin, growth factor, cytokine, antioxidant, 2-mercaptoethanol, pyruvic acid, buffering agent, inorganic salts and so on.

To avoid complicated preparation, a serum-free medium supplemented with an appropriate amount (e.g., about 0.5% to about 30%, preferably about 1% to about 20%) of commercially available KSR (manufactured by Life Technologies) may be used as such serum-free medium (e.g., medium of 1:1 mixture of F-12 medium and IMDM medium supplemented with 10% KSR and 450 µM 1-monothioglycerol). As a product equivalent to KSR, the medium disclosed in JP-A-2001-508302 can be mentioned.

The "serum-containing medium" in the present invention means a medium containing unadjusted or unpurified serum. The medium may contain a fatty acid, lipid, amino acid (e.g., non-essential amino acids), vitamin, growth factor, cytokine, antioxidant, 2-mercaptoethanol, 1-monothioglycerol, pyruvic acid, buffering agent, inorganic salts and so on. For example, a serum medium can be used in the step of maintaining the retinal cell or retinal tissue produced by the present invention (Cell Stem Cell, 10(6), 771-775 (2012)).

In the present invention, the culturing is preferably performed under xeno-free conditions. The "xeno-free" means conditions eliminating components derived from species different from that of the cell to be cultured.

In the present invention, the "medium containing substance X" or "in the presence of substance X" refer to a medium supplemented with an exogenous substance X or a medium containing an exogenous substance X, or in the presence of an exogenous substance X. That is, when the cells or tissues present in the medium endogenously express, secrete or produce substance X, the endogenous substance X is distinguished from the exogenous substance X, and a medium free of exogenous substance X is understood to fall outside the category of the "medium containing substance X", even when it contains endogenous substance X.

For example, a "medium containing a factor for maintaining an undifferentiated state" is a medium supplemented with an exogenous factor for maintaining an undifferentiated state or a medium containing an exogenous factor for maintaining an undifferentiated state.

In the present invention, a feeder cell refers to a cell other than a stem cell co-exist when culturing the stem cell. Examples of the feeder cells used for culturing pluripotent stem cells while maintaining an undifferentiated state include mouse fibroblasts (MEF), human fibroblasts, SNL cells and the like. As the feeder cells, feeder cells that underwent a growth suppression treatment is preferable. Examples of the growth suppression treatment include treatment with a growth inhibitor (e.g., mitomycin C), gamma radiation, UV irradiation and the like. Feeder cells used for culturing pluripotent stem cells while maintaining an undifferentiated state contributes to the maintenance of undifferentiation of pluripotent stem cell by secretion of a humoral factor (preferably factor for maintaining an undifferentiated state), or production of a scaffold for cell adhesion (extracellular substrate).

In the present invention, the absence of feeder cells (under feeder-free conditions means culturing in the absence of a feeder cell. The absence of feeder cells means, for example, conditions free of addition of feeder cells, or conditions substantially free of feeder cells (e.g., the ratio of the number of feeder cells relative to the total number of cells is not more than 3%).

In the present invention, an "aggregate" of cells refers to a clump formed by assembly of cells dispersed in a medium, wherein the cells are adhered to each other. Cell clumps, embryoid bodies, spheres, spheroids are also encompassed in the cell aggregates. Preferably, a planar cell-cell adhesion is formed in the aggregate of cells. In some embodiments, cells sometimes form a cell-cell junction and/or a cell adhesion, for example, adherence junction, in some or all of the aggregates. The "aggregate" in the present invention specifically includes an aggregate produced in the second step of the above-mentioned present invention [1], which is formed by cells dispersed at the time of the start of the suspension culturing, and an aggregate produced in the third step of the above-mentioned present invention [1], which contains induced retinal cells differentiated from pluripotent stem cell, and the "aggregate" also includes an aggregate already formed at the time of the start of the second step in the above-mentioned present invention [1] (i.e., at the time of the start of suspension culture). The cell aggregate formed in the second step encompasses "embryoid body (EB)".

In the present invention, "uniformed aggregates" means that the size of each aggregate is constant when a plurality of aggregates are cultured, and that the variance in the length of the maximum diameter is small when the size of the aggregates are evaluated by the length of the maximum diameter. More specifically, it means that not less than 75% of aggregates in the whole aggregate population are within mean±100%, preferably mean±50%, more preferably mean±20%, of the maximum diameter in the population of the aggregates.

In the present invention, to "form uniformed cell aggregates" means to "rapidly aggregate a given number of dispersed cells" to form cell aggregates uniform in size, when gathering the cells to form cell aggregates and culturing the aggregates in suspension.

Dispersion refers to dividing cells or a tissue into small cell clumps (not less than 2 cells and not more than 100 cells, preferably not more than 50 cells) or single cells by a dispersion treatment such as enzymatic treatment, physical treatment and the like. A given number of dispersed cells is a collection of a certain number of cell clumps or single cells.

Examples of the method of dispersing pluripotent stem cells include mechanical dispersion treatment, cell dispersion solution treatment, and cell protecting agent addition treatment. These treatments may be performed in combination. Preferably, cell dispersion treatment is performed and then mechanical dispersion treatment is performed.

As a method of mechanical dispersion treatment, pipetting treatment or scraping operation by a scraper can be mentioned.

As a cell dispersion solution to be used for the cell dispersion solution treatment, a solution containing any of enzymes such as trypsin, collagenase, hyaluronidase, elastase, pronase, DNase, papain and so on, and a chelating agent such as ethylenediaminetetraacetic acid and so on can be mentioned. A commercially available cell dispersion solution such as TripLE Select (manufactured by Life Technologies) and TripLE Express (manufactured by Life Technologies) can also be used.

When pluripotent stem cells are dispersed or until dispersed cells form an aggregate, the cell death of pluripotent stem cells that have not formed an aggregate may be suppressed by a treatment with a cell protecting agent. As a cell protecting agent to be used for the cell protecting agent treatment, an FGF signal transduction pathway activating substance, heparin, Rho-associated coiled-coil kinase (ROCK) inhibitor, serum, or serum replacement can be mentioned. As a preferable cell protecting agent, a ROCK inhibitor can be mentioned. As a ROCK inhibitor, Y-27632, Fasudil or H-1152 can be mentioned. While the concentration of a ROCK inhibitor can be appropriately set by those of ordinary skill in the art, for example, it can be set within a concentration range corresponding to a ROCK inhibitory activity with about 50 nM-200 µM of Y-27632.

For example, a method for dispersing pluripotent stem cells includes, for example, a method involving treating a colony of pluripotent stem cells with a cell dispersion solution (TripLE Select) in the presence of a ROCK inhibitor as a cell protecting agent, and further dispersing them by pipetting.

In the production method of the present invention, it is preferable to form an aggregate of pluripotent stem cells by rapidly gathering the pluripotent stem cells. When an aggregate of pluripotent stem cells is formed in such a manner, an epithelium-like structure can be formed with good reproducibility in the cells induced and differentiated from the formed aggregate. Examples of the experimental operation to form an aggregate include a method involving keeping cells in a small space by using a plate with small wells (e.g., plate with wells having a base area of about 0.1-2.0 cm$^2$ when calculated in terms of flat bottom), micropore and so on, a method involving aggregating cells by centrifugation for a short time using a small centrifugation tube. As a plate with small wells, for example, 24 well plate (area of about 1.88 cm$^2$ when calculated in terms of flat bottom), 48 well plate (area of about 1.0 cm$^2$ when calculated in terms of flat bottom), 96 well plate (area of about 0.35 cm$^2$ when calculated in terms of flat bottom, inner diameter about 6-8 mm), and 384 well plate can be mentioned. Preferred is 96 well plate. As a shape of the plate with small wells, the shape of the bottom surface when the well is seen from above is, for example, polygon, rectangle, ellipse, true circle, preferably true circle. As a shape of the plate with small wells when the well is seen from the side well, the shape of the bottom surface is preferably a structure having high outer circumference and low inner concave. For example, U-bottom, V-bottom, µ-bottom can be mentioned, preferably U-bottom or V-bottom, more preferably V-bottom. As a plate with small wells, a cell culture dish (e.g., 60 mm-150 mm dish, culture flask) with a concave convex, or dent (e.g., EZSPHERE (Asahi Techno Glass)) on the bottom surface may also be used. The bottom surface of a plate with small wells is preferably a non-cell-adhesive bottom surface, preferably the aforementioned non-cell-adhesive-coated bottom surface.

Formation of aggregates of pluripotent stem cells and formation of an epithelial-like structure in the aggregate can be confirmed based on the macroscopic morphology of the aggregate, microscopic morphology by tissue staining analysis, distribution of cells expressing differentiation and undifferentiation markers and the like.

The "tissue" in the present invention refers to a structure of a cell population having a structure in which plural types of cells having different morphologies and properties are sterically arranged in a given pattern.

In the present invention, the "retinal tissue" means a tissue in which at least two or more types of cells such as photoreceptor cells, horizontal cells, bipolar cells, amacrin cells, retinal ganglion cells, their progenitor/progenitor cells, and retinal progenitor cells and so on, which constitute respective retinal layers in retina in vivo, are sterically arranged in layers. The retinal layer which is constituted by each cell can be confirmed by a known method, for example, presence or absence of the expression of a cell marker or the level thereof, etc.

The "retinal layer" in the present invention means each layer constituting the retina. Specific examples thereof include retinal pigment epithelial layer, photoreceptor layer, external limiting membrane, outer nuclear layer, outer plexiform layer, inner nuclear layer, inner plexiform layer, ganglion cell layer, nerve fiber layer and inner limiting membrane.

The "retinal progenitor cell" in the present invention refers to a progenitor cell capable of differentiating into any mature retinal cell including photoreceptor cell, horizontal cell, bipolar cell, amacrine cell, retinal ganglion cell, retinal pigment epithelial cell and the like.

The photoreceptor progenitor cell, horizontal cell progenitor cell, bipolar cell progenitor cell, amacrine cell progenitor cell, retinal ganglion cell progenitor cell, and retinal pigment epithelial progenitor cell refer to progenitor cells committed to differentiate into photoreceptor cell, horizontal cell, bipolar cell, amacrine cell, retinal ganglion cell, and retinal pigment epithelial cell, respectively.

In the present invention, the "retinal layer-specific neuron" is a cell constituting a retina layer and is a neuronal cell specific to the retinal layer. Examples of the retinal layer-specific neuron include bipolar cell, retinal ganglion cell, amacrine cell, horizontal cell and photoreceptor cell, and examples of the photoreceptor cell include rod cell and cone cell.

The "retinal cell" in the present invention encompasses the aforementioned retinal progenitor cell, retinal layer specific neuron and progenitor cell of retinal layer specific neuron.

Examples of the retinal cell marker include Rx (also referred to as Rax), PAX6 and Chx10 expressed in retinal progenitor cell, Nkx2.1 expressed in progenitor cell of hypothalamus neuron but not expressed in retinal progenitor cell, Sox1 expressed in hypothalamus neuroepithelium but not expressed in retina, Crx and Blimp1 expressed in progenitor cell of photoreceptor cell, and the like. Examples of the marker of the retinal layer-specific neuron include Chx10, PKCα and L7 expressed in bipolar cell, TUJI and Brn3 expressed in retinal ganglion cell, Calretinin expressed in amacrine cell, Calbindin expressed in horizontal cell, Rhodopsin and Recoverin expressed in mature photoreceptor cell, Nrl expressed in rod cell, Rxr-gamma expressed in cone cell, RPE65 and Mitf expressed in retinal pigment epithelium cell and the like.

2. Method for Producing Retinal Cells or a Retinal Tissue

The production method of the present invention is a method for producing a retinal cell or a retinal tissue, comprising the following steps:
(1) a first step of culturing a mammalian pluripotent stem cell in the absence of a feeder cell for a period not exceeding 30 days in a medium comprising 1) a factor for maintaining an undifferentiated state and 2) an MEK inhibitor,
(2) a second step of culturing the cells obtained in the first step in suspension to form a cell aggregate, and
(3) a third step of culturing the aggregate obtained in the second step in suspension in the presence of a BMP signal transduction pathway activating substance to obtain an aggregate containing a retinal cell or a retinal tissue.
(1) The First Step As a preferable pluripotent stem cell in the first step, induced pluripotent stem cell, more preferably human induced pluripotent stem cell can be mentioned. The production method of induced pluripotent stem cells is not particularly limited, and it can be produced by a method well known to those of ordinary skill in the art as mentioned above. It is also desirable to perform a step for preparing induced pluripotent stem cells (that is, a step of reprogramming somatic cells to establish pluripotent stem cells) under feeder-free condition.

The maintenance culturing or expansion culturing for obtaining pluripotent stem cells to be used in the first step can be performed by a method well known to those of ordinary skill in the art as mentioned above. While the maintenance culturing and expansion culturing of pluripotent stem cells can be performed by adhesion culturing or suspension culturing, it is preferably performed by adhesion culturing. While the step of maintenance culturing and expansion culturing of pluripotent stem cells may be performed in the presence of a feeder or under feeder-free condition, it is preferably performed under feeder-free condition.

The production method of the present invention may comprise, before step (1), a step of maintaining a pluripotent stem cell under feeder-free conditions and providing the pluripotent stem cell maintained under feeder-free conditions. While the period of maintaining under feeder-free conditions is not particularly limited as long as retinal cells or retinal tissues are produced by the method of the present invention, it is generally not less than one day, preferably not less than 3 days, more preferably not less than 7 days. There is no theoretical upper limit in the maintaining period under feeder-free conditions, and pluripotent stem cells can be semipeimanently cultured and expanded while maintaining pluripotency under appropriate culture conditions and under feeder-free conditions. However, when pluripotent stem cells are maintained for a long term, the risk of their differentiation and loss of pluripotency may increase. Therefore, the period for maintaining under feeder-free conditions is, for example, within 6 months, preferably within about 3 months, and the passage number is, for example, within 30 passages, preferably within 20 passages. The maintenance culture under feeder-free conditions can be performed under culture conditions of the first step described in detail below except that the medium does not contain an MEK inhibitor, a PKC inhibitor or a B-Raf inhibitor.

When the pluripotent stem cells that underwent maintenance culturing or expansion culturing under feeder-free conditions are recovered, dispersed pluripotent stem cells are prepared by a dispersion operation. A dispersion operation of the pluripotent stem cells include mechanical dispersion treatment, cell dispersion solution treatment or cell protecting agent addition treatment, mentioned earlier. These treatments may be performed in combination. Preferably, cell dispersion treatment is performed simultaneously with cell protecting agent addition treatment, and then mechanical dispersion treatment is performed.

As a cell protecting agent used for the cell protecting agent addition treatment, heparin, serum and serum replacement can be mentioned. To suppress cell death induced by dispersion (particularly, cell death of human pluripotent stem cells), a Rho-associated coiled-coil kinase (ROCK) inhibitor may be added at the time of dispersion. As a ROCK inhibitor, Y-27632, Fasudil (HA1077), H-1152 and the like can be mentioned.

As a cell dispersion solution to be used for the cell dispersion treatment, a solution containing any of enzymes such as trypsin, collagenase, hyaluronidase, elastase, pronase, DNase, papain and so on, and a chelating agent such as ethylenediaminetetraacetic acid and so on can be mentioned. A commercially available cell dispersion solution such as TrypLE Select (manufactured by Life Technologies) and TrypLE Express (manufactured by Life Technologies) can also be used.

As a method of the mechanical dispersion treatment, a pipetting treatment or scraping by a scraper can be mentioned.

The dispersed pluripotent stem cells are seeded in a new culture container and subjected to the first step.

To suppress cell death induced by dispersion (particularly, cell death of human pluripotent stem cells), the pluripotent stem cells may be seeded in a new culture container, maintenance culturing may be continuously performed under feeder-free conditions in the presence of a ROCK inhibitor, and the first step may be started thereafter. While the period of the treatment with a ROCK inhibitor is not particularly limited as long as the cell death induced by dispersion can be suppressed, it is generally about 12-24 hr.

The factor for maintaining an undifferentiated state is not particularly limited as long as it is a substance having an action to suppress differentiation of pluripotent stem cells. It is generally a factor for maintaining an undifferentiated state derived from a mammal. Since the factor for maintaining an undifferentiated state may have cross-reactivity among mammal species, a factor for maintaining an undifferentiated state of any mammal may also be used as long as the undifferentiated state of the pluripotent stem cells to be cultured can be maintained. Preferably, a factor for maintaining an undifferentiated state of a mammal of the same species as the cells to be cultured is used.

Examples of the factor for maintaining an undifferentiated state widely used by those of ordinary skill in the art include an FGF signal transduction pathway activating substance, a TGFβ family signal transduction pathway activating substance and the like in the case of primed pluripotent stem cells (e.g., human ES cells, human iPS cells). As the FGF signal transduction pathway activating substance, fibroblast growth factors (e.g., bFGF, FGF4, FGF8) can be specifically mentioned. As the TGFβ family signal transduction pathway activating substance, a TGFβ signal transduction pathway activating substance, a Nodal/Activin signal transduction pathway activating substance can be mentioned. As the TGFβ signal transduction pathway activating substance, TGFβ1, TGFβ2 can be mentioned. As the Nodal/Activin signal transduction pathway activating substance, Nodal, Activin A, Activin B can be mentioned. When human pluripotent stem cells (human ES cells, human iPS cells) are cultured, the factor for maintaining an undifferentiated state is preferably bFGF.

The factor for maintaining an undifferentiated state to be used in the present invention is preferably isolated. Being "isolated" means that an operation to remove factors other than the intended component or cell has been performed, and the component or cell is no longer in a naturally occurring state. Therefore, "isolated protein X" does not include an endogenous protein X produced from the cells or tissue to be cultured, and contained in a cell or tissue or in the medium. The purity of the "isolated protein X" (percentage of the weight of protein X to the total protein weight) is generally not less than 70%, preferably not less than 80%, more preferably not less than 90%, further preferably not less than 99%, most preferably 100%. Therefore, in one embodiment, the present invention comprises a step of providing an isolated factor for maintaining an undifferentiated state.

In one embodiment, it includes a step of exogenously adding an isolated factor for maintaining an undifferentiated state to a medium used in the first step. Alternatively, a factor for maintaining an undifferentiated state may be added in advance to a medium to be used in the first step. To be specific, the aforementioned basal medium supplemented with an undifferentiated maintenance factor or a commercially available medium containing an undifferentiated maintenance factor for culturing undifferentiated cells such as stem cell or iPS cell and the like can be used in the first step.

The concentration of the factor for maintaining an undifferentiated state in the medium to be used in the first step is a concentration capable of maintaining the undifferentiated state of the pluripotent stem cells to be cultured, and can be appropriately determined by those of ordinary skill in the art. For example, specifically, when bFGF is used as a factor for maintaining an undifferentiated state in the absence of a feeder cell, the concentration thereof is generally about 4 ng-500 ng/mL, preferably 10 ng-200 ng/mL, more preferably about 30 ng-150 ng/mL.

The MEK inhibitor is not particularly limited as long as it is a substance that inhibits expression or activity of MEK family, and may be any of protein, nucleic acid and low-molecular-weight compound. As the representative MEK family, MEK1, MEK2, MEK3 and the like can be mentioned, and the MEK inhibitor is a substance that inhibits the expression or activity of one, a plurality or all of these MEK families. Examples of the substance include, but are not limited to, substances (e.g., antisense oligonucleotide, siRNA etc.) that suppress expression of genes encoding various MEKs and substances that inhibit enzyme activity of various MEKs. Specific Examples of the MEK inhibitor include, but are not limited to, low-molecular-weight compounds such as PD0325901 (N-[(2R)-2,3-dihydroxypropoxy-3,4-difluoro-2-[(2-fluoro-4-Iodophenyl)amino]-benzamide), PD184352 (2-(2-chloro-4-indophenylamino)-N-cyclopropylmethoxy-3,4-difluorobenzamido), PD98059 (2'-amino-3'-methoxyflavone), U0126 (1.4-diamino-2,3-di-cyano-1,4-bis[2-amino-phenylthio]butadiene), MEK162 (5-[(4-Bromo-2-fluorophenyl)amino]-4-fluoro-N-(2-hydroxyethoxy)-1-methyl-1H-benzimidazole-6-carboxamide), SL327 (α-[amino[(4-aminophenyl)thio]methylene]-2-(trifluoromethyl)benzeneacetonitrile) and the like. PD0325901, PD184352, PD98059, U0126, MEK162 and SL327 are known MEK inhibitors and commercially available products and the like can be obtained as appropriate. As the MEK inhibitor, preferred is PD0325901, PD184352 or U0126, and more preferred is PD0325901.

In the method of the present invention, the concentration of the MEK inhibitor contained in the medium is not particularly limited as long as a retinal cell or retinal tissue of a mammal can be produced by the method of the present invention, and can be appropriately determined according to the kind of the MEK inhibitor. For example, the concentration of the MEK inhibitor is in a concentration range showing an MEK inhibitory activity corresponding to 0.001-10 μM, preferably 0.005-5 μM, particularly preferably 0.01-2.5 μM, of PD0325901.

In the method of the present invention, the medium used in the first step may contain a PKC inhibitor or a B-Raf inhibitor as well as a factor for maintaining an undifferentiated state and an MEK inhibitor. Addition of a PKC inhibitor or a B-Raf inhibitor is expected to improve production efficiency of a cell aggregate capable of differentiating into retinal cells, or retinal cells and retinal tissues.

The PKC inhibitor is not particularly limited as long as it is a substance capable of inhibiting expression or activity of protein kinase C (PKC), and may be any of protein, nucleic acid and low-molecular-weight compound. PKC here is a protein family constituted of at least 10 kinds of isozymes, and the PKC inhibitor is a substance that inhibits the expression or activity of one, a plurality or all of these PKC families. Examples of the substance include, but are not limited to, a substance that suppresses expression of a gene encoding PKC (e.g., antisense oligonucleotide, siRNA etc.), a substance that inhibits enzyme activity of PKC [for example, low-molecular-weight compounds such as Go6983 (wherein "o" is umlaut) (3-[1-[3-(Dimethylamino)propyl]-5-methoxy-1H-indol-3-yl]-4-(1H-indol-3-yl)-1H-pyrrole-2,5-dione) and the like, and the like] and the like. Go6983 is a known PKC inhibitor, and can be obtained easily since it is commercially available. As the PKC inhibitor, preferred is Go6983.

In the method of the present invention, when the medium in the first step contains a PKC inhibitor, the concentration of the PKC inhibitor contained in the medium is not particularly limited as long as the method of the present invention can produce a retinal cell or a retinal tissue of a mammal, and can be appropriately determined according to the kind of the PKC inhibitor. The concentration of the PKC inhibitor is, for example, within a concentration range showing a PKC inhibitory activity corresponding to 0.05-10 μM, preferably 0.25-5 μM, more preferably 0.5-2.5 μM, of Go6983.

B-Raf inhibitor is not particularly limited as long as it is a substance that suppresses expression or serine/threonine kinase activity of B-Raf and may be any of protein, nucleic acid and low-molecular-weight compound. Examples of the substance include, but are not limited to, a substance that suppresses expression of a gene encoding B-Raf (e.g., antisense oligonucleotide, siRNA etc.), a substance that suppresses enzyme activity of B-Raf [for example, low-molecular-weight compounds such as anti-B-Raf antibody, SB590885 (5-[2-[4-[2-(dimethylamino)ethoxy]phenyl]-5-(4-pyridinyl)-1H-imidazol-4-yl]-2,3-dihydro-1H-inden-1- one oxime) and the like, and the like] and the like. B-Raf inhibitor is preferably SB590885.

In the method of the present invention, when the medium in the first step contains a B-Raf inhibitor, the concentration of the B-Raf inhibitor contained in the medium is not particularly limited as long as the method of the present invention can produce a retinal cell or a retinal tissue of a mammal, and can be appropriately determined according to the kind of the B-Raf inhibitor. For example, the concentration of the B-Raf inhibitor is within a concentration range showing a B-Raf inhibitory activity corresponding to 0.05-10 μM, preferably 0.25-5 μM, more preferably 0.5-2.5 μM, of SB590885.

In the first step, a pluripotent stem cell may be cultured under any conditions of suspension culturing and adhesion culturing, preferably adhesion culturing.

A medium to be used in the first step may be a serum-containing medium or a serum-free medium. To avoid contamination with chemically-undefined components, it is preferably a serum-free medium, more preferably, a serum-free medium containing the aforementioned serum replacement.

To avoid contamination of chemically-undefined components, the medium used in the first step is preferably a medium containing chemically-determined components.

The medium used in the first step is not particularly limited as long as it contains 1) a factor for maintaining an undifferentiated state, and 2) an MEK inhibitor (and optionally 3) a PKC inhibitor or a B-Raf inhibitor) and enables undifferentiated maintenance culture of pluripotent stem cells under feeder-free conditions (feeder-free medium).

In the first step, in the absence of a feeder cell (feeder-free conditions) means conditions substantially free of a feeder cell (e.g., the ratio of number of feeder cells relative to the total number of cells is not more than 3%).

As the feeder-free medium, many synthetic media have been developed and are commercially available and, for example, Essential 8 medium can be mentioned. Essential 8 medium is DMEM/F12 medium containing L-ascorbic acid-2-phosphate magnesium (64 mg/l), sodium selenium (14 μg/l), insulin (19.4 mg/l), NaHCO$_3$ (543 mg/l), transferrin (10.7 mg/l), bFGF (100 ng/mL), and a TGFβ family signal transduction pathway activating substance (TGFβ 1 (2 ng/mL) or Nodal (100 ng/mL)) as additives (Nature Methods, 8, 424-429 (2011)). Examples of the commercially available feeder-free medium include Essential 8 (manufactured by Life Technologies), S-medium (manufactured by DS Pharma Biomedical), StemPro (manufactured by Life Technologies), hESF9 (Proc Natl Acad Sci USA. 2008 Sep. 9; 105(36):13409-14), mTeSR1 (manufactured by STEMCELL Technologies), mTeSR2 (manufactured by STEMCELL Technologies), and TeSR-E8 (manufactured by STEMCELL Technologies). In addition to these, StemFit (manufactured by Ajinomoto Co., Inc.) can be mentioned as the feeder-free medium. The present invention can be performed using any of these media added with (i) an MAP kinase kinase inhibitor (MEK inhibitor) or a medium added with (ii) an MEK inhibitor and a PKC inhibitor or B-Raf inhibitor in the above-mentioned first step. In one embodiment, in the above-mentioned first step, any of these media added with an MEK inhibitor, a medium added with an MEK inhibitor and a PKC inhibitor or a medium added with an MEK inhibitor and a B-Raf inhibitor can be mentioned.

The medium used in the first step contains an MEK inhibitor in addition to a factor for maintaining an undifferentiated state. Alternatively, the medium used in the first step contains an MEK inhibitor, and a PKC inhibitor or a B-Raf inhibitor in addition to a factor for maintaining an undifferentiated state. For example, (i) a medium containing a factor for maintaining an undifferentiated state and an MEK inhibitor, and not containing a PKC inhibitor and a B-Raf inhibitor, (ii) a medium containing a factor for maintaining an undifferentiated state and MEK inhibitor and not containing a PKC inhibitor, a B-Raf inhibitor, a TGFβ family signal transduction pathway inhibitor and a Sonic hedgehog signal transduction pathway activating substance, (iii) a medium containing a factor for maintaining an undifferentiated state, an MEK inhibitor, and a PKC inhibitor or a B-Raf inhibitor, (iv) a medium containing a factor for maintaining an undifferentiated state, an MEK inhibitor, and a PKC inhibitor or a B-Raf inhibitor, and not containing a TGFβ family signal transduction pathway inhibitor and a Sonic hedgehog signal transduction pathway activating substance, and the like are used.

By subjecting the pluripotent stem cells to suspension culture in the second step after the first step, the state of the cells changes and cell aggregates can be produced with high efficiency. For example, by subjecting the pluripotent stem cells to suspension culture in the second step after the first step, the state of the cells changes and the quality of the aggregates is improved. Thus, round cell aggregates with a smooth surface and dense inside are expected to be produced with high efficiency. The medium to be used in the first step can contain a further component (e.g., any activating substance or inhibitor of signal transduction pathway) as long as the production efficiency of retinal cells or retinal tissues by the production method of the present invention is not markedly decreased (e.g., the same level as or not more than the level of efficiency without the first step).

For culturing pluripotent stem cells under feeder-free conditions in the first step, an appropriate matrix may be used as a scaffold to provide a scaffold in stead of the feeder cells to the pluripotent stem cells. The pluripotent stem cells are subjected to adhesion culturing in a cell container whose surface is coated with a matrix as a scaffold.

As a matrix available as a scaffold, laminin (Nat Biotechnol 28, 611-615 (2010)), laminin fragment (Nat Commun 3, 1236 (2012)), basement membrane preparation (Nat Biotechnol 19, 971-974 (2001)), gelatin, collagen, heparan sulfate proteoglycan, entactin, vitronectin and the like can be mentioned.

"Laminin" is a heterotrimer molecule consisting of α, β, γ chains and an extracellular matrix protein containing isoforms having different subunit chain compositions. Specifically, laminin has about 15 kinds of isoforms based on the combinations of heterotrimers with 5 kinds of α chains, 4 kinds of β chains and 3 kinds of γ chains. The name of laminin is determined by combining respective numbers of α chain (α1-α5), β chain (β1-β4) and γ chain (γ1-γ3). For example, a laminin having a combination of α5 chain, β1 chain, γ1 chain is named laminin 511. In the present invention, laminin 511 is preferably used (Nat Biotechnol 28, 611-615 (2010)).

Laminin to be used in the present invention is generally a mammalian laminin. As the mammal, those mentioned above can be recited. To achieve xeno-free conditions, laminin of a mammal of the same species as the cell to be cultured is preferably used. For example, human laminin (preferably, human laminin 511) is used for culturing human pluripotent stem cells.

A laminin fragment to be used in the present invention is not particularly limited as long as it has adhesiveness to pluripotent stem cells and enables maintenance culturing of pluripotent stem cell under feeder-free conditions, and is preferably E8 fragment. Laminin E8 fragment (laminin511-E8) was identified as a fragment with strong cell adhesion activity among the fragments obtained by digestion of laminin 511 with elastase (EMBO J., 3:1463-1468, 1984, J. Cell Biol., 105:589-598, 1987). In the present invention, E8 fragment of laminin 511 is preferably used (Nat Commun 3, 1236 (2012), Scientific Reports 4, 3549 (2014)). The laminin E8 fragment to be used in the present invention is not required to be an elastase-digestion product of laminin and may be a recombinant. To avoid contamination of unidentified components, a recombinant laminin fragment is preferably used in the present invention. A E8 fragment of laminin 511 is commercially available and, for example, iMatrix-511 (Nippi, Inc.) and the like can be purchased.

The laminin or laminin fragment to be used in the present invention is preferably isolated.

The "basement membrane preparation (basement membrane specimen)" in the present invention refers to one containing basement membrane-constituting components having a function to control cell morphology, differentiation, growth, motility, expression of function and so on which are similar to those of epithelial cell, when intended cells capable of forming a basement membrane are plated thereon and cultured. For example, retinal cells and retinal tissues produced by the present invention may be dispersed, and cultured in the presence of a basement membrane preparation when further adhesion culturing is performed. Here, the "basement membrane constituting components" refers to extracellular matrix molecules in the form of a thin membrane present between epithelial cell layer and interstitial cell layer and so on in animal tissues. A basement membrane preparation can be produced by, for example, removing cells capable of forming a basement membrane, which adhere onto a support via a basement membrane, from a support with a solution capable of dissolving the lipid of the cells, an alkali solution and so on. Examples of the basement membrane preparation include products commercially available as basement membrane preparation (e.g., Matrigel™ (manufactured by Becton Dickinson: hereinafter sometimes referred to as Matrigel)), Geltrex™ (manufactured by Life Technologies), and extracellular matrix molecules known as basement membrane components (e.g., laminin, type IV collagen, heparan sulfate proteoglycan, entactin and so on). Matrigel™ is a basement membrane preparation extracted from Engelbreth Holm Swarn (EHS) mouse sarcoma. The main component of Matrigel™ is type IV collagen, laminin, heparan sulfate proteoglycan, and entactin. In addition to these, TGF-β, FGF, tissue plasminogen activator, and a growth factor naturally produced by EHS tumor are contained. The "growth factor reduced product" of Matrigel™ has a lower growth factor concentration than common Matrigel™, and the standard concentration thereof is <0.5 ng/ml for EGF, <0.2 ng/ml for NGF, <5 µg/ml for PDGF, 5 ng/ml for IGF1, and 1.7 ng/ml for TGFβ.

To avoid contamination of unidentified components, an isolated laminin or laminin fragment is preferably used in the present invention.

Preferably, in the culturing of pluripotent stem cells under feeder-free conditions in the first step, the human pluripotent stem cells are cultured in an adhered state in a cell container with surface coated with isolated laminin 511 or E8 fragment of laminin 511 (most preferably, E8 fragment of laminin 511).

While the period for the culturing of pluripotent stem cells in the first step is not particularly limited as long as the effect of improving the quality of the aggregate formed in a second step can be achieved, it is generally a period not exceeding 30 days, preferably 0.5-8 days, more preferably 1-6 days, further preferably 4-6 days. That is, the first step is started 30 days, preferably 0.5-8 days, more preferably 1-6 days, further preferably 4-6 days before the start of the second step, and the second step is continuously performed on completion of the first step.

In one embodiment, when the medium in the first step contains a factor for maintaining an undifferentiated state and an MEK inhibitor and does not contain both a PKC inhibitor a B-RAF inhibitor (e.g., does not contain other factors possibly influencing differentiation induction), the culture period of the pluripotent stem cells in the first step is set to 4-6 days (e.g., 5 days).

In one embodiment, when the medium in the first step contains a factor for maintaining an undifferentiated state, an MEK inhibitor and a PKC inhibitor or a B-RAF inhibitor, the culture period of the pluripotent stem cells in the first step is set to 1-6 days (e.g., 1-5 days).

The culture conditions such as culture temperature, and $CO_2$ concentration in the first step can be appropriately determined. While the culture temperature is, for example, about 30° C. to about 40° C., preferably about 37° C. The $CO_2$ concentration is, for example, about 1% to about 10%, preferably about 5%.

In a preferable embodiment, the cell population obtained in the first step is a cell population containing cells maintaining pluripotent-like properties (pluripotent-like state). In this sense, it can be said a cell population maintaining pluripotent-like properties. The pluripotent-like properties mean that at least a part of the characteristics unique to and common to the pluripotent stem cells including pluripotency is maintained. The pluripotent-like properties do not require strict pluripotency. Specifically, a state expressing all or some of the markers to be the index of pluripotent properties (pluripotent state) is included in the "pluripotent-like properties". As a marker (undifferentiated marker) of the pluripotent-like properties, Oct3/4 positive, alkaline phosphatase positive and the like can be mentioned. In one embodiment, a cell maintaining the pluripotent-like properties is Oct3/4 positive. Even if the expression level of Nanog is lower than that of ES cell or iPS cell, it corresponds to "cell showing pluripotent-like properties". That is, while the first step is not the culture condition capable of maintaining the undifferentiated state of pluripotent stem cells, it is conducted under culturing conditions capable of maintaining pluripotent-like properties enabling differentiation into at least plural types of ectodermal cells. The pluripotent-like properties are maintained throughout the first step.

The cells obtained in the first step have an ability to differentiate into retinal cells and retinal tissues. In one embodiment, the cells obtained in the first step are stem cells having an ability to differentiate into retinal cells (including retinal progenitor cells, retina layer specific nerve cells and progenitor cells thereof) and retinal tissues.

In a preferable embodiment, human pluripotent stem cells (e.g., iPS cells) are adhesion cultured in the absence of a feeder cell in (i) a serum-free medium containing an MEK inhibitor and bFGF, or (ii) a serum-free medium containing an MEK inhibitor, a PKC inhibitor or a B-Raf inhibitor, and bFGF. A specific combination includes a combination of an MEK inhibitor (e.g., PD0325901) and bFGF; a combination of an MEK inhibitor (e.g., PD0325901), a PKC inhibitor (e.g., Go6983) and bFGF; a combination of an MEK inhibitor (e.g., PD0325901), a B-Raf inhibitor (e.g., SB590885) and bFGF, and the like.

The above-mentioned adhesion culture is preferably performed in a cell container with a surface coated with laminin 511 or E8 fragment of laminin 511.

For example, human pluripotent stem cells (e.g., human iPS cells) are maintenance cultured in the absence of a feeder cell and in a serum-free medium containing bFGF. The maintenance culture is preferably performed in adhesion culturing. The adhesion culturing is preferably performed in a cell container with a surface coated with vitronectin, laminin 511 or E8 fragment of laminin 511. To the culture thereof is added (i) an MEK inhibitor or (ii) a combination of an MEK inhibitor and a PKC inhibitor or a B-Raf inhibitor (specifically, PD0325901; combination of PD0325901 and Go6983; combination of PD0325901 and SB590885 and the like can be mentioned) and culturing is continued.

The cells thus-obtained in the first step have an ability to differentiate into at least retinal tissues, retinal cells, retinal progenitor cells, or retina layer specific nerve cells. Preferably, the cells thus-obtained in the first step include stem cells having an ability to differentiate into at least retinal tissues, retinal cells, retinal progenitor cells, or retina layer specific nerve cells.

[2] The Second Step

The second step of culturing the cells obtained in the first step in suspension in a medium to form a cell aggregate is explained.

The medium to be used in the second step is not particularly limited as long as it is as described in the above-mentioned section of definition. The medium to be used in the second step may be a serum-containing medium or serum-free medium. To avoid contamination of chemically-undefined components, a serum-free medium not added with any of a factor for maintaining an undifferentiated state, an MEK inhibitor, a PKC inhibitor and a B-Raf inhibitor can be used in the present invention. To avoid complicated preparation, for example, a serum-free medium supplemented with an appropriate amount of a commercially available serum replacement such as KSR and so on (e.g., medium of 1:1 mixture of IMDM and F-12, which is supplemented with 10% KSR, 450 µM 1-monothioglycerol and 1× Chemically Defined Lipid Concentrate, or GMEM medium supplemented with 5%-20% KSR, NEAA, pyruvic acid, 2-mercaptoethanol) is preferably used. The amount of KSR to be added to a serum-free medium in the case of human pluripotent stem cells is, for example, about 1% to about 30%, preferably about 2% to about 20%.

For formation of an aggregate, the dispersed cells are prepared by a dispersing operation of the cells obtained in the first step. The "dispersed cells" obtained by the dispersing operation refers to a cell population in which, for example, not less than 70% of cells are single cells and not more than % of cells are clumps of 2-50 cells. Preferably, it is a cell population of dispersed cells in which not less than 80% of the cells are single cells, and not more than 20% of the cells are clumps of 2-50 cells. In one embodiment, the dispersed cells refer to a cell population in a state almost free of mutual adhesion of cells (e.g., plane attachment). In some of the embodiments, dispersed cells refer to a cell population in a state almost free of cell-cell junction (e.g., adhesive bond).

A dispersion operation of the cells obtained in the first step may contain the above-mentioned mechanical dispersion treatment, cell dispersion solution treatment, and cell protecting agent addition treatment. These treatments may be performed in combination. Preferably, cell dispersion solution treatment is performed simultaneously with cell protecting agent addition treatment and then mechanical dispersion treatment is performed.

As a cell protecting agent to be used for the cell protecting agent addition treatment, heparin, serum and serum replacement can be mentioned. Also, to suppress cell death of pluripotent stem cells (particularly, human pluripotent stem cells) induced by dispersion, a Rho-associated coiled-coil kinase (ROCK) inhibitor or a Myosin inhibitor may be added from the start of the second step culture. As a ROCK inhibitor, Y-27632, Fasudil (HA1077), H-1152 and the like can be mentioned.

As a cell dispersion solution to be used for the cell dispersion treatment, a solution containing any of enzymes such as trypsin, collagenase, hyaluronidase, elastase, pronase, DNase, papain and so on, and a chelating agent such as ethylenediaminetetraacetic acid and so on can be mentioned. A commercially available cell dispersion solution such as TrypLE Select (manufactured by Life Technologies) and TrypLE Express (manufactured by Life Technologies) can also be used.

As a method of the mechanical dispersion treatment, pipetting treatment or scraping by a scraper can be mentioned.

The dispersed cells are suspended in the above-mentioned medium.

Then, a suspension of the dispersed cells is seeded in the above-mentioned culture vessel, and the dispersed cells are cultured under a condition non-adhesive to the culture vessel, whereby plural cells are gathered to form an aggregate.

In this case, plural cell aggregates may be simultaneously formed in one culture vessel by seeding the dispersed cells in a comparatively large culture vessel such as a 10 cm dish. However, the size of the aggregates varies in this case. Thus, for example, a given amount of the cells are placed in each well of a multiwell plate (U-bottom, V-bottom) such as a 96-well microplate, and static culture is performed, whereby the cells are rapidly coagulated to form one aggregate in each well. The aggregates are recovered from plural wells, whereby a population of uniformed aggregates can be obtained.

The concentration of the cells in the second step can be appropriately set so that cell aggregates can be more uniformly and efficiently formed. For example, when human cells (e.g., cells obtained from human iPS cells in the first step) are cultured in suspension using a 96-well microwell plate, a liquid prepared to achieve about $1 \times 10^3$ to about $1 \times 10^5$ cells, preferably about $3 \times 10^3$ to about $5 \times 10^4$ cells, more preferably about $4 \times 10^3$ to about $2 \times 10^4$ cells, further preferably about $4 \times 10^3$ to about $1.6 \times 10^4$ cells, most preferably about $8 \times 10^3$ to about $1.2 \times 10^4$ cells, per well is added to the wells, and the plate is left to stand to form aggregates.

The culture conditions such as culture temperature, $CO_2$ concentration and so on in the second step can be appropriately determined. The culture temperature is, for example, about ° C. to about 40° C., preferably about 37° C. The $CO_2$ concentration is, for example, about 1% to about 10%, preferably about 5%.

In the second step, when a medium change operation is performed, for example, an operation to add a fresh medium without discarding the existing medium (medium addition operation), an operation to discard about a half amount of the existing medium (about 30-90%, for example, 40-60% of the volume of the existing medium) and add about a half amount of a fresh medium (30-90%, for example, about 40-60% of the volume of the existing medium) (half-medium change operation), and an operation to discard about the whole amount of the existing medium (not less than 90% of the amount of the existing medium) and add about the whole amount of a fresh medium (not less than 90% of the amount of the existing medium) (full-medium change operation) can be mentioned.

When a particular component is added at a certain time point, for example, an operation to calculate the final concentration, to discard about a half amount of the existing medium, and to add about a half amount of a fresh medium containing a particular component at a concentration higher than the final concentration (half-medium change operation) may be performed.

When the concentration of a component contained in the existing medium is to be decreased by dilution at a certain time pointed, for example, the medium change operation may be performed plural times per day, preferably plural times (e.g., 2-3 times) within 1 hr. Also, when the concentration of a component contained in the existing medium is to be decreased by dilution at a certain time point, the cells or aggregates may be transferred to another culture container.

While the tool used for the medium change operation is not particularly limited, for example, pipetter, micropipette, multichannel micropipette, continuous dispenser, and the like can be mentioned. For example, when a 96 well plate is used as a culture vessel, a multichannel micropipette may be used.

The period for suspension culturing necessary forming a cell aggregate can be determined as appropriate according to the cell to be used, so that the cells can be aggregated uniformly. To form uniformed cell aggregates, it is desirably as short as possible. The steps for the dispersed cells to form cell aggregates can be divided into a step for gathering cells, and a step forming cell aggregates from the gathered cells. At the time point of seeding the dispersed cells (i.e., at the time of the start of suspension culture) to gather the cells in case of human pluripotent stem cells (e.g., stem cells obtained from human iPS cells in the first step), for example, the gathered cells are formed preferably within about 24 hr, more preferably within about 12 hr. The period from the time point of seeding the dispersed cells (i.e., at the time of the start of suspension culture) to the formation of an aggregate in the case of human pluripotent stem cells (e.g., human iPS cells) is, for example, preferably within about 72 hr, more preferably within about 48 hr. The period for cell aggregate formation can be appropriately adjusted by controlling the tools for aggregating the cells, centrifugation conditions and so on.

Formation of cell aggregates can be determined based on the size and cell number of the aggregates, macroscopic morphology, microscopic morphology by tissue staining analysis and uniformity thereof, expression of differentiation- and undifferentiation-markers and uniformity thereof, control of expression of differentiation marker and synchronism thereof, reproducibility of differentiation efficiency between the aggregates, and so on.

After aggregate formation, the aggregate may be continuously cultured as it is. The period for suspension culturing in the second step is generally 12 hr-6 days, preferably about 12 hr-48 hr.

In one embodiment, the medium used in the second step contains a Sonic hedgehog signal transduction pathway activating substance. That is, in the second step, the cells obtained in the first step are cultured in suspension in a medium (preferably serum-free medium) containing a Sonic hedgehog signal transduction pathway activating substance, whereby a cell aggregate having further improved quality of the aggregate can be formed at a high efficiency. For example, round cell aggregates with a smooth surface and dense inside and having further improved quality of aggregate and maintaining shape are expected to be produced with high efficiency.

The Sonic hedgehog (hereinafter sometimes to be indicated as Shh) signal transduction pathway activating substance is a substance capable of enhancing signal transduction mediated by Shh. Examples of the Shh signal transduction pathway activating substance include proteins belonging to the Hedgehog family (e.g., Shh and Ihh), Shh receptor, Shh receptor agonist, Purmorphamine or SAG (Smoothened Agonist; N-methyl-N'-(3-pyridinylbenzyl)-N'-(3-chlorobenzo[b]thiophene-2-carbonyl)-1,4-diaminocyclohexane) and the like. The Shh signal transduction pathway activating substance is preferably SAG.

The Sonic hedgehog signal transduction promoting activity of SAG can be determined by a method well known to those of ordinary skill in the art, for example, reporter gene assay taking note of the expression of Gli1 gene (Oncogene (2007) 26, 5163-5168).

The concentration of the Sonic hedgehog signal transduction pathway activating substance in the medium can be appropriately determined to fall within a range capable of achieving the aforementioned effects. SAG is generally used at a concentration of 1-2000 nM, preferably 1-1000 nM, preferably 10 nM-700 nM, 20 nM-500 nM, further preferably 100 nM-500 nM. When a Sonic hedgehog signal transduction pathway activating substance other than SAG is used, it is desirably used at a concentration conferring Sonic hedgehog signal transduction promoting activity equivalent to that of SAG at the above-mentioned concentration.

The timing of addition of a Sonic hedgehog signal transduction pathway activating substance to the medium is not particularly limited as long as the above-mentioned effects can be afforded, but a higher effect can be obtained when it is added earlier. A Sonic hedgehog signal transduction pathway activating substance is added to the medium generally within 6 days, preferably within 3 days, more preferably within 1 day, from the start of the second step, and most preferably at the time of the start of the second step.

The concentration of the Sonic hedgehog signal transduction pathway activating substance in the medium may be varied during the period of the second step. For example, the Sonic hedgehog signal transduction pathway activating substance is provided to fall within the above-mentioned range at the time of the start of the second step, and the concentration may be gradually or stepwisely decreased at a ratio of 40-60% per 2-4 days.

In a preferable embodiment, in the second step, the human cells obtained in the first step (e.g., cells obtained from human iPS cells in the first step) are recovered, dispersed into single cells or a state close thereto and subjected to suspension culturing in a serum-free medium containing a Sonic hedgehog signal transduction pathway activating substance (e.g., SAG) to form aggregates. A Sonic hedgehog signal transduction pathway activating substance is preferably contained in the medium from the time of the start of suspension culture. A ROCK inhibitor (e.g., Y-27632) may also be added to the medium. The period for the culturing is 12 hr-6 days, preferably 12 hr-48 hr. The aggregates formed are preferably uniformed aggregates.

For example, the human cells obtained in the first step (e.g., cells obtained from human iPS cell in the first step) are recovered, dispersed into single cells or a state close thereto in a serum-free medium containing a Sonic hedgehog signal transduction pathway activating substance (e.g., SAG), and subjected to suspension culturing. The serum-free medium may contain a ROCK inhibitor (e.g., Y-27632). A suspension of the cells obtained from human pluripotent stem cells (e.g., iPS cells) is seeded in the above-mentioned non-adhesive culture vessel, whereby plural cells are assembled to form an aggregate. The period for the culturing is 12 hr-6 days, preferably 12 hr-48 hr. The aggregates formed are preferably uniformed aggregates.

It is also within the scope of the present invention to culture aggregates in suspension in the absence of a basement membrane preparation.

In a preferable embodiment, when the medium in the first step contains a factor for maintaining an undifferentiated state and an MEK inhibitor and does not contain either a PKC inhibitor or a B-RAF inhibitor (e.g., does not contain other factors possibly influencing differentiation induction), a medium containing a Sonic hedgehog signal transduction pathway activating substance (e.g., SAG) is used in the second step. That is, a production method of a retinal cell or retinal tissue including the following steps is provided:
(1) a first step of culturing mammalian pluripotent stem cells in the absence of a feeder cell in a medium containing 1) a factor for maintaining an undifferentiated state and 2) an MEK inhibitor, and not containing 3) either a PKC inhibitor or a B-RAF inhibitor (e.g., does not contain other factors possibly influencing differentiation induction) for a period not exceeding 30 days, preferably 0.5-8 days, more preferably 1-6 days,
(2) a second step of culturing in suspension the cells obtained in the first step in a serum-free medium containing a Sonic hedgehog signal transduction pathway activating substance to form an aggregate of the cells, and
(3) a third step of culturing in suspension the aggregate obtained in the second step in the presence of a BMP signal transduction pathway activating substance to give an aggregate containing retinal cells or a retinal tissue.

In a preferable embodiment, when the medium in the first step contains a factor for maintaining an undifferentiated state and an MEK inhibitor and does not contain either a PKC inhibitor or a B-RAF inhibitor (e.g., does not contain other factors possibly influencing differentiation induction), the culture period of the first step is 4-6 days (e.g., 5 days) and a medium not containing a Sonic hedgehog signal transduction pathway activating substance (e.g., SAG) is used in the second step. That is, a production method of a retinal cell or retinal tissue including the following steps is provided:
(1) a first step of culturing mammalian pluripotent stem cells in the absence of a feeder cell in a medium containing 1) a factor for maintaining an undifferentiated state and 2) an MEK inhibitor, and not containing 3) either a PKC inhibitor or a B-RAF inhibitor (e.g., does not contain other factors possibly influencing differentiation induction) for 4-6 days (e.g., 5 days)
(2) a second step of culturing in suspension the cells obtained in the first step in a serum-free medium not containing a Sonic hedgehog signal transduction pathway activating substance to form an aggregate of the cells, and
(3) a third step of culturing in suspension the aggregate obtained in the second step in the presence of a BMP signal transduction pathway activating substance to give an aggregate containing retinal cells or a retinal tissue.

In a preferable embodiment, when the medium in the first step contains a factor for maintaining an undifferentiated state, an MEK inhibitor and a PKC inhibitor or a B-RAF inhibitor (e.g., medium containing a factor for maintaining an undifferentiated state, an MEK inhibitor, and a PKC inhibitor or B-RAF inhibitor, and not containing other factors possibly influencing differentiation induction), a medium containing or not containing a Sonic hedgehog signal transduction pathway activating substance (e.g., SAG) is used in the second step. That is, a production method of a retinal cell or retinal tissue including the following steps is provided:
(1) a first step of culturing mammalian pluripotent stem cells in the absence of a feeder cell in a medium containing 1) a factor for maintaining an undifferentiated state, 2) an MEK inhibitor, and 3) either a PKC inhibitor or a B-RAF inhibitor (e.g., medium containing 1) a factor for maintaining an undifferentiated state, 2) an MEK inhibitor, and 3) either a PKC inhibitor or a B-RAF inhibitor, and not containing 4) other factors possibly influencing differentiation induction) for a period not exceeding 30 days,
(2) a second step of culturing the cells obtained in the first step in suspension in a serum-free medium containing or not containing a Sonic hedgehog signal transduction pathway activating substance (e.g., SAG) to form a cell aggregate, and
(3) a third step of culturing the aggregate obtained in the second step in suspension in the presence of a BMP signal transduction pathway activating substance to give an aggregate containing retinal cells or a retinal tissue.

By performing the second step in this manner, an aggregate of the cells obtained in the first step, or the cells derived therefrom is formed. The present invention also provides a method for producing such aggregate. The aggregate obtained in the second step has higher quality than the one formed without a treatment in a medium containing (i) an MEK inhibitor or (ii) an MEK inhibitor, and a PKC inhibitor or B-Raf inhibitor in the first step. Thus, the present invention provides a method of producing a cell aggregate with an improved quality with high efficiency. To be specific, for example, a population of aggregates having a high ratio of round cell aggregates having a smooth surface, a dense inside, and uncollapsed shape can be expected to be obtained. In one embodiment, when aggregates (e.g., not less than 100 aggregates) are randomly selected on day 6, preferably day 10, from the start of the second step, the sum of the ratios of uncollapsed aggregates and/or non-cystic aggregates is, for example, not less than 70%, preferably not less than 80%.

The aggregate obtained in the second step has an ability to differentiate into a retinal cell (including retinal progenitor cell, retina layer specific nerve cell and progenitor cell thereof) or a retinal tissue containing them.

Using, in the second step, the cells obtained in the first step and having an ability to differentiate into a retinal cell (including retinal progenitor cell, retina layer specific nerve cell and progenitor cell thereof) or a retinal tissue containing them, an aggregate containing cells having an ability to differentiate into a retinal cell (including retinal progenitor cell, retina layer specific nerve cell and progenitor cell thereof) or a retinal tissue containing them can be obtained. Since the aggregate obtained in the second step has high quality, various retinal cells and retinal tissues can be induced with high efficiency by culturing the aggregate under appropriate differentiation conditions.

In one embodiment, using, in the second step, the stem cells (preferably, cells having an ability to differentiate into at least retinal tissue, retinal cell, retinal progenitor cell, or retina layer specific nerve cell) obtained in the first step and having an ability to differentiate into at least retinal cells (including retinal progenitor cell, retina layer specific nerve cell and progenitor cell thereof) or a retinal tissue containing them, an aggregate containing cells having an ability to differentiate into at least retinal cells (including retinal progenitor cell, retina layer specific nerve cell and progenitor cell thereof) or a retinal tissue containing them can be obtained.

In one embodiment, the aggregate obtained in the second step contains cells maintaining pluripotent-like properties (specifically, expressing Oct3/4) obtained on completion of the first step, and/or cells corresponding to the cells in an intermediate stage between the cells and neural cells such as retinal cells and the like. These cells express any of pluripotent state marker Oct3/4, ectoderm marker (Sox1, Sox2, N-cadherin, TP63), neuroectoderm marker (Sox1, Sox2, Nestin, N-cadherin, TP63, Otx2), and the aforementioned neural cell marker. That is, in one embodiment, the aggregate obtained in the second step contains a mixture of cells expressing any of pluripotent state marker Oct3/4, ectoderm marker (Sox1, Sox2, N-cadherin, TP63), neuroectoderm marker (Sox1, Sox2, Nestin, N-cadherin, TP63, Otx2), and the aforementioned neural cell marker. That is, the aggregate obtained in the second step contains stem cells having a potency to differentiate into at least a retinal cell or retinal tissue, and/or progenitor cells of a retinal cell or retinal tissue. The progenitor cells are characterized in that they show an ability (competence) to express the aforementioned retinal cell markers when they are cultured under known appropriate culture conditions. Therefore, in one embodiment, the aggregate obtained in the second step contains Oct3/4 positive stem cells having a potency to differentiate into at least a retinal cell or retinal tissue, and/or progenitor cells of a retinal cell or retinal tissue. A part of the cells contained in the aggregate obtained in the second step may express the aforementioned retinal tissue markers.

The aggregate obtained in the second step has a potency to differentiate into retinal cells and retinal tissues. An aggregate containing retinal cells and retinal tissues can be produced with high efficiency by culturing the aggregate obtained in the second step under the following conditions of the third step since the aggregate has high quality.

[3] The Third Step

A third step where an aggregate containing retinal cells or a retinal tissue are induced from the aggregate obtained in the second step is explained.

The medium to be used in the third step is, for example, a serum-free medium or a serum-containing medium (preferably serum-free medium) supplemented with a BMP signal transduction pathway activating substance. Such medium may or may not contain a basement membrane preparation. As the basement membrane preparation, those mentioned above can be used. When a basement membrane preparation is added, the concentration thereof is, for example, 0.1 to 10%, more preferably 0.5% to 2%, in volume concentration when Matrigel is used. To avoid contamination with a chemically unidentified substance, a basement membrane preparation is not added. That is, the present invention encompasses a culture method in which the suspension culture in the third step is performed in the absence of a basement membrane preparation.

A serum-free medium or serum-containing medium to be used for such medium is not particularly limited as long as it is as mentioned above. To avoid complicated preparation, for example, a serum-free medium supplemented with an appropriate amount of a commercially available serum replacement such as KSR and so on (e.g., medium of 1:1 mixture of IMDM and F-12 supplemented with 10% KSR, 450 µM 1-monothioglycerol and 1× Chemically Defined Lipid Concentrate) is preferably used. The amount of KSR to be added to a serum-free medium in the case of cells derived from human pluripotent stem cell (e.g., iPS cell) is generally about 1% to about 20%, preferably about 2% to about 20%.

As the medium (preferably serum-free medium) to be used in the third step, the medium (preferably serum-free medium) used in the second step may be directly used, or may be replaced with a fresh medium (preferably serum-free medium). When the serum-free medium used in the second step free of a BMP signal transduction pathway activating substance is directly used for the third step, a BMP signal transduction pathway activating substance may be added to the medium.

Examples of BMP signal transduction pathway activating substance used in the third step include BMP proteins such as BMP2, BMP4, BMP7 etc., GDF proteins such as GDF7 etc., anti-BMP receptor antibody, BMP partial peptides and so on. BMP2 protein, BMP4 protein and BMP7 protein are available from, for example, R&D Systems, and GDF7 protein is available from, for example, Wako Pure Chemical Industries, Ltd. The BMP signal transduction pathway activating substance is preferably BMP4.

The concentration of the BMP signal transduction pathway activating substance may be a concentration at which differentiation of the cells forming the above-mentioned aggregates into retinal cells can be induced. For example, in the case of human BMP4, it is added to the medium to a concentration of about 0.01 nM to about 1 µM, preferably about 0.1 nM to about 100 nM, more preferably about 1.5 nM (55 ng/mL). When a BMP signal transduction pathway activating substance other than BMP4 is used, it is desirably used at a concentration at which a BMP signal transduction promoting activity equivalent to that of BMP4 at the above-mentioned concentration is exerted.

The concentration of the BMP signal transduction pathway activating substance in the medium may be varied during the period of the third step. For example, the BMP signal transduction pathway activating substance is provided to fall within the above-mentioned range of a concentration at the time of the start of the third step, and the concentration may be gradually or stepwise decreased at a ratio of 40-60% per 2-4 days.

A BMP signal transduction pathway activating substance may be added after about 24 hr or later from the start of the suspension culturing in the second step, and may also be added to the medium within several days (e.g., within 15 days) from the start of the suspension culturing. Preferably, a BMP signal transduction pathway activating substance is added to the medium at any time point between day 1 and day 15, more preferably between day 1 and day 9, further preferably between day 3 and day 8, still more preferably, between day 3 and day 6, from the start of the suspension culture.

After the addition of a BMP signal transduction pathway activating substance to the medium and the start of the differentiation induction of cells forming an aggregate into retinal cells, addition of the BMP signal transduction pathway activating substance to the medium is not necessary, and the medium may be exchanged with a serum-free medium or serum-containing medium each free of a BMP signal transduction pathway activating substance. In one embodiment, after the start of the differentiation induction into retinal cells, the concentration of the BMP signal transduction pathway activating substance in the medium is gradually or stepwisely decreased at a ratio of 40-60% per 2-4 days by exchanging the medium with a serum-free medium or a serum-containing medium, each free of a BMP signal transduction pathway activating substance. The cells whose induction of differentiation into retinal cells has been started can be confirmed by, for example, detecting the expression of retinal progenitor cell marker gene (e.g., Rx gene (alias Rax), Pax6 gene, Chx10 gene) in the cells. The aggregate formed in the second step by using pluripotent stem cells in which a fluorescence reporter protein gene such as GFP and so on is knocked-in into the Rx gene locus is cultured in suspension in the presence of a BMP signal transduction pathway activating substance at a concentration necessary for differentiation induction into retinal cell, and fluorescence emitted from the expressed fluorescence reporter protein is detected, whereby the time point when differentiation induction into retinal cell was started can be confirmed. As one embodiment of the third step, a step of culturing the aggregate formed in the second step in suspension in a serum-free medium or serum-containing medium containing a BMP signal transduction pathway activating substance at a concentration necessary for differentiation induction into retinal cell, until a cell expressing retinal progenitor cell marker gene (e.g., Rx gene, Pax6 gene, Chx10 gene) begins appearing, thereby obtaining a cell aggregate comprising retinal progenitor cells can be mentioned.

In the third step, when a medium change operation is performed, for example, an operation to add a fresh medium without discarding the existing medium (medium addition operation), an operation to discard about a half amount of the existing medium (about 40-80% of the volume of the existing medium) and add about a half amount of a fresh medium (40-80% of the volume of the existing medium) (half-medium change operation), and an operation to discard about the whole amount of the existing medium (not less than 90% of the amount of the existing medium) and add about the whole amount of a fresh medium (not less than 90% of the amount of the existing medium) (full-medium change operation) can be mentioned.

When a particular component (e.g., BMP4) is added at a certain time point, for example, based on the calculation of the final concentration, an operation to discard about a half amount of the existing medium, and to add about a half amount of a fresh medium containing a particular component at a concentration higher than the final concentration (half-medium change operation) may be performed.

When the concentration of a component contained in the existing medium is to be decreased by dilution at a certain time pointed, for example, the medium change operation may be performed plural times per day, preferably plural times (e.g., 2-3 times) within 1 hr. Also, when the concentration of a component contained in the existing medium is to be decreased by dilution at a certain time point, the cell or aggregate may be transferred to another culture container.

While the tool used for the medium change operation is not particularly limited, for example, pipetter, micropipette, multichannel micropipette, continuous dispenser, and the like can be mentioned. For example, when a 96 well plate is used as a culture vessel, a multichannel micropipette may be used.

In one embodiment, when the concentration of the Shh signal transduction pathway activating substance added to the medium in the second step is comparatively low (e.g., not more than 700 nM for SAG, and a concentration conferring Shh signal transduction promoting activity equivalent to or lower than that of SAG at the above-mentioned concentration, for other Shh signal transduction pathway activating substances), medium change is not necessary, and in the third step, a BMP signal transduction pathway activating substance may be added to the medium used in the second step.

On the other hand, when the concentration of the Shh signal transduction pathway activating substance is comparatively high (e.g., exceeding 700 nM, preferably not less than 1000 nM for SAG, and a concentration conferring a Shh signal transduction promoting activity equivalent to that of SAG at the above-mentioned concentration, for other Shh signal transduction pathway activating substances), it is desirable to change the medium to a fresh medium containing a BMP signal transduction pathway activating substance (e.g., BMP4) to suppress an effect of the Shh signal transduction pathway activating substance remaining when a BMP signal transduction pathway activating substance is added.

In a preferable embodiment, the concentration of a Shh signal transduction pathway activating substance in the medium to be used in the third step is, when calculated in terms of Shh signal transduction promoting activity of SAG, not more than 700 nM, preferably not more than 300 nM, more preferably not more than 10 nM, further preferably not more than 0.1 nM, most preferably free of a Shh signal transduction pathway activating substance. The medium "free of a Shh signal transduction pathway activating substance" also includes a medium substantially free of a Shh signal transduction pathway activating substance, for example, a medium not supplemented with a Shh signal transduction pathway activating substance at a concentration imparting an adverse influence on selective differentiation into a retinal progenitor cell or a retinal tissue. The medium "not supplemented with a Shh signal transduction pathway activating substance" also includes a medium substantially not supplemented with a Shh signal transduction pathway activating substance, for example, a medium not supplemented with a Shh signal transduction pathway activating substance at a concentration imparting an adverse effect on selective differentiation into a retinal progenitor cell or a retinal tissue.

The culture conditions such as culture temperature, $CO_2$ concentration and so on in the third step can be appropriately determined. The culture temperature is, for example, about 30° C. to about 40° C., preferably about 37° C. The $CO_2$ concentration is, for example, about 1% to about 10%, preferably about 5%.

By such culturing, differentiation of the cells forming the aggregate obtained in the second step into retinal progenitor cells is induced, whereby an aggregate containing the retinal progenitor cells can be obtained. The present invention also provides a method for producing such aggregate containing retinal progenitor cells. That an aggregate comprising retinal progenitor cells was obtained can be confirmed by, for example, detecting the presence of cells expressing Rax, PAX6 or Chx10, which is a retinal progenitor cell marker, in the aggregate. One embodiment of the third step is a step of culturing the aggregate formed in the second step in suspension in a serum-free medium or serum-containing medium containing a BMP signal transduction pathway activating substance at a concentration necessary for differentiation induction into a retinal cell, until a cell expressing Rx gene begins appearing, whereby obtaining an aggregate comprising retinal progenitor cells. In one embodiment, the culturing of the third step is performed until not less than 20% (preferably, not less than 30%, not less than 40%, not less than 50%, not less than 60%) of the cells contained in the aggregate express Rx.

In one embodiment, in the aggregate obtained in the third step, the proportion of the aggregates expressing Rx on day 18 to day 25, for example, day 22, from the start of the second step is, for example, not less than 60%, preferably not less than 80%.

In one embodiment, in the aggregate obtained in the second step, the proportion of the aggregates expressing Pax6 and/or Chx10 on day 18 to day 25, for example, day 22, from the start of the second step is, for example, not less than 60%, preferably not less than 80%.

In a preferable embodiment in the production of retinal progenitor cells and/or retinal tissues, human pluripotent stem cells (e.g., human iPS cells) are subjected to adhesion culture in the absence of a feeder cell in a serum-free medium containing bFGF, an MEK inhibitor (e.g., PD0325901) and a PKC inhibitor (e.g., Go6983) for a period not exceeding 30 days, preferably 0.5 day-8 days, more preferably 1 day-6 days in the first step; the cells obtained in the first step are subjected to suspension culture in a serum-free medium containing a Sonic hedgehog signal transduction pathway activating substance (e.g., SAG) to form cell aggregates in the second step; and the aggregates obtained in the second step are subjected to suspension culture in a serum-free medium containing an BMP signal transduction pathway activating substance (e.g., BMP4) in the third step.

In another preferable embodiment in the production of retinal cells and/or retinal tissues, human pluripotent stem cells (e.g., human iPS cells) are subjected to adhesion culture in the absence of a feeder cell in a serum-free medium containing bFGF, an MEK inhibitor (e.g., PD0325901) and a B-Raf inhibitor (e.g., SB590885) for a period not exceeding 30 days, preferably 0.5 day-8 days, more preferably 1 day-6 days in the first step; the cells obtained in the first step are subjected to suspension culture in a serum-free medium containing a Sonic hedgehog signal transduction pathway activating substance (e.g., SAG) to form cell aggregates in the second step; and the aggregates obtained in the second step are subjected to suspension culture in a serum-free medium containing an BMP signal transduction pathway activating substance (e.g., BMP4) in the third step.

In a preferable embodiment in the production of retinal progenitor cells and/or retinal tissues, human pluripotent stem cells (e.g., human iPS cells) are subjected to adhesion culture in the absence of a feeder cell in a serum-free medium containing bFGF and an MEK inhibitor (e.g., PD0325901) and not containing a PKC inhibitor (e.g., Go6983) or a B-Raf inhibitor (e.g., SB590885) for a period not exceeding 30 days, preferably 0.5 day-8 days, more preferably 1 day-6 days, further preferably 4 days-6 days in the first step; the cells obtained in the first step are subjected to suspension culture in a serum-free medium not containing a Sonic hedgehog signal transduction pathway activating substance (e.g., SAG) to form cell aggregates in the second step; and the aggregates obtained in the second step are subjected to suspension culture in a serum-free medium containing an BMP signal transduction pathway activating substance (e.g., BMP4) in the third step.

In addition, in a preferable embodiment in the production of retinal progenitor cells and/or retinal tissues, human pluripotent stem cells (e.g., human iPS cells) are subjected to adhesion culture in the absence of a feeder cell in a serum-free medium containing bFGF and an MEK inhibitor (e.g., PD0325901) and not containing a PKC inhibitor (e.g., Go6983) or a B-Raf inhibitor (e.g., SB590885) for a period not exceeding 30 days, preferably 0.5 day-8 days, more preferably 1 day-6 days, in the first step; the cells obtained in the first step are subjected to suspension culture in a serum-free medium containing a Sonic hedgehog signal transduction pathway activating substance (e.g., SAG) to form cell aggregates in the second step; and the aggregates obtained in the second step are subjected to suspension culture in a serum-free medium containing an BMP signal transduction pathway activating substance (e.g., BMP4) in the third step.

The obtained aggregate containing retinal progenitor cells may be used as it is as a reagent for evaluating toxicity or efficacy. An aggregate containing retinal progenitor cells is subjected to a dispersion treatment (e.g., trypsin/EDTA treatment or papain treatment), and the obtained cells are subjected to a selection using FACS or MACS, whereby highly pure retinal progenitor cells can also be obtained.

Furthermore, the aggregate containing retinal progenitor cells may be continuously cultured in a serum-free medium or serum-containing medium to produce a neuroepithelial structure-like retinal tissue containing retina layer specific nerve cells.

A serum-free medium or serum-containing medium to be used for such medium is not particularly limited as long as it is as mentioned above. For example, a serum-containing medium which is a DMEM-F12 medium supplemented with 10% fetal bovine serum, N2 supplement, 100 µM taurine, and 500 nM retinoic acid, or a serum-free medium supplemented with an appropriate amount of a commercially available serum replacement such as KSR and so on (e.g., medium of 1:1 mixture of IMDM and F-12 supplemented with 10% KSR, 450 µM 1-thioglycerol (or thioglycerol) and 1× Chemically Defined Lipid Concentrate) and the like can be mentioned.

While the period for the culturing for inducing a retinal tissue containing retina layer specific nerve cells from retinal progenitor cells varies depending on the intended retinal layer-specific neurons, it is, for example, about 7 days to about 200 days.

The retinal tissue exists covering the surface of the aggregate. After completion of the suspension culturing, the aggregate may be fixed with a fixative such as para-formaldehyde solution and so on, and a cryosection is prepared, then formation of a retinal tissue having a layer structure may be confirmed by immunostaining and the like. Since respective layers of a retinal tissue are composed of different precursors of retina layer specific nerve cells (photoreceptor cell, horizontal cell, bipolar cell, amacrine cell, retinal ganglion cell), formation of a layer structure can be confirmed using antibodies against the aforementioned markers expressed in these cells by the immunostaining. In one embodiment, the retinal tissue is an Rx- or Chx10-positive neuroepithelial structure.

The retinal tissue existing on the surface of the aggregate can be physically cut out from the aggregate by using tweezers and the like. In this case, since a neural tissue other than the retinal tissue may be formed on the surface of each aggregate, a part of the neural tissue cut out from the aggregate may be subjected to confirmation by the below-mentioned immunostaining and the like, whereby the tissue can be confirmed to be a retinal tissue.

In one embodiment, the aggregate obtained in the third step contains a retinal tissue and is substantially free of non-neural head ectoderm. In an aggregate containing a retinal tissue and substantially free of non-neural head ectoderm, for example, an Rx-positive tissue is observed and an Rx-negative tissue is not observed on the outside thereof in the immunostaining images of the aforementioned aggregate frozen section.

One embodiment of the third step is a step of culturing the aggregate formed in the second step in suspension in a serum-free medium or serum-containing medium containing a BMP signal transduction pathway activating substance at a concentration necessary for differentiation induction into retinal cells, until a cell expressing Rx or Pax6 gene begins appearing to give an aggregate comprising retinal progenitor cells, and subsequently culturing the aggregate containing the retinal progenitor cells in suspension in a serum-free medium or serum-containing medium until a retinal tissue is formed, whereby obtaining an aggregate comprising a retinal tissue. When the aggregate containing the retinal progenitor cells is subsequently cultured in suspension in a serum-free medium or serum-containing medium until a retinal tissue is formed, the concentration of the BMP signal transduction pathway activating substance in the medium in order to induce retinal progenitor cells may be gradually or stepwisely decreased at a ratio of 40-60% per 2-4 days by exchanging the medium with a serum-free medium or a serum-containing medium, each not supplemented with a BMP signal transduction pathway activating substance. In one embodiment, suspension culturing of an aggregate containing retinal progenitor cells is performed until not less than 20% (preferably, not less than 30%, not less than 40%, not less than 50%, not less than 60%) of the cells contained in the aggregate expresses Chx10.

In one embodiment of the third step, the aggregate obtained in the second step, or an aggregate obtained by culturing the aggregate obtained in the second step in suspension by the above-mentioned method may be subjected to adhesion culturing to form an adhered aggregate. The adhered aggregate is cultured in an adhered state in a serum-free medium or serum-containing medium containing a BMP signal transduction pathway activating substance at a concentration necessary for differentiation induction into a retinal cell, until a cell expressing Rx or Pax6 gene begins appearing to give an aggregate containing retinal progenitor cells. The aggregate containing the retinal progenitor cells is cultured in an adhered state in a serum-free medium or serum-containing medium until a retinal tissue is formed, whereby an aggregate containing a retinal tissue is obtained. In one embodiment, adhesion culturing of the aggregate containing retinal progenitor cells is performed until not less than 10% (preferably, not less than 20%, not less than 30%, not less than 40%, not less than 50%) of the cells express Chx10.

By the production method of the present invention, a retinal tissue can be obtained with high efficiency from pluripotent stem cells. Since the retinal tissue obtained by the production method of the present invention contains neurons specific to each of the retinal layers, it is also possible to obtain cells constituting a retinal tissue, such as photoreceptor cell, horizontal cell, bipolar cell, amacrine cell, retinal ganglion cell or a progenitor cell thereof and the like. Which cell was obtained from the obtained retinal tissue can be confirmed by a method known per se, for example, expression of a cell marker.

The obtained aggregate containing a retinal tissue may also be directly used as a reagent for evaluating toxicity or efficacy. An aggregate containing a retinal tissue is subjected to a dispersion treatment (e.g., trypsin/EDTA treatment), and the obtained cells are subjected to a selection using FACS or MACS, whereby highly pure retinal tissue-constituting cells, for example, highly pure photoreceptor cells, can also be obtained.

A ciliary marginal zone-like structure can be produced by a method well known to those of ordinary skill in the art from the cell aggregate containing a retinal tissue, which is obtained by the production method of the present invention (e.g., WO 2013/183774, WO 2015/087614, WO 2015/107738). Specifically, the method described in the following step (A) and step (B) can be mentioned.

The ciliary marginal zone-like structure in the present invention refers to a structure similar to a ciliary marginal zone. Examples of the "ciliary marginal zone (CMZ)" include a tissue present in the boundary region of retinal tissue (specifically, neural retina) and retinal pigment epithelium in the retina in vivo, which is a region containing tissue stem cells of retina (retinal stem cells). Ciliary marginal zone is also called a ciliary margin or retinal margin, and the ciliary marginal zone, ciliary margin and retinal margin are equivalent tissues. It is known that the ciliary marginal zone plays an important role in the supply of retinal progenitor cells or differentiated cells to retinal tissues, maintenance of retinal tissue structure and so on. Examples of the marker gene of the ciliary marginal zone include Rdh10 gene (positive), Otx1 gene (positive), Zic1 (positive) and so on.

Step (A) comprises culturing a cell aggregate comprising a retinal tissue obtained by the production method 2 of the present invention in which Chx10 positive cells are present in a proportion of 20% or more and 100% or less of the retinal tissue, in a serum-free medium or serum-containing medium each containing a Wnt signal pathway activating substance and/or an FGF signal pathway inhibitor for only a period before the appearance of a RPE65 gene-expressing cell.

As a preferable culturing of step (A) here, suspension culturing can be mentioned.

As a serum-free medium to be used in step (A), a serum-free medium which is a basal medium supplemented with N2 or KSR can be mentioned. More specifically, a serum-free medium which is a DMEM/F-12 medium supplemented with N2 supplement (manufactured by Life Technologies Corporation) can be mentioned. As the serum-containing medium, a serum-containing medium which is a basal medium supplemented with fetal bovine serum can be mentioned.

The culture conditions of step (A) such as culture temperature, $CO_2$ concentration can be appropriately set. The culture temperature is, for example, in the range of about 30° C. to about 40° C., preferably, for example, around about 37° C. The $CO_2$ concentration is, for example, in the range of about 1% to about 10%, preferably, for example, around about 5%.

In step (A), the Wnt signal transduction pathway activating substance to be contained in a serum-free medium or serum-containing medium when the above-mentioned "cell aggregate comprising a retinal tissue" is cultured in the medium is not particularly limited as long as it can enhance signal transduction mediated by Wnt. Specific examples of the Wnt signal transduction pathway activating substance include a protein belonging to Wnt family (e.g., Wnt1, Wnt3a, Wnt7a), Wnt receptor, Wnt receptor agonist, GSK3β inhibitor (e.g., 6-Bromoindirubin-3'-oxime (BIO), CHIR99021, Kenpaullone) and so on.

The concentration of the Wnt signal transduction pathway activating substance to be contained in a serum-free medium or serum-containing medium in step (A) in the case of a common Wnt signal transduction pathway activating substance such as CHIR99021 is, for example, in the range of about 0.1 µM to about 100 µM, preferably, for example, in the range of about 1 µM to about 30 µM, more preferably, for example, around 3 µM.

The FGF signal transduction pathway inhibitor to be contained in a serum-free medium or serum-containing medium in step (A) when the above-mentioned "cell aggregate comprising a retinal tissue" is cultured in the medium is not particularly limited as long as it can inhibit signal transduction mediated by FGF. Examples of the FGF signal transduction pathway inhibitor include FGF receptor, FGF receptor inhibitor (e.g., SU-5402, AZD4547, BGJ398), MAP kinase cascade inhibitor (e.g., MEK inhibitor, MAPK inhibitor, ERK inhibitor), PI3 kinase inhibitor, Akt inhibitor and so on.

The concentration of the FGF signal transduction pathway inhibitor contained in a serum-free medium or serum-containing medium in step (A) only needs to be a concentration at which differentiation of an aggregate into ciliary marginal zone-like structure can be induced. For example, in the case of SU-5402, it is added to the medium at a concentration of about 0.1 µM to about 100 µM, preferably about 1 µM to about 30 µM, more preferably about 5 µM.

"Culturing for only a period before the appearance of a RPE65 gene-expressing cell" in step (A) means culturing in the whole or a part of the period before the appearance of a RPE65 gene-expressing cell. That is, culturing in the whole or a part of the period (any period) during which the aforementioned "cell aggregate comprising a retinal tissue" in the culture system is constituted by cells that do not substantially express RPE65 gene suffices. By employing such culturing, a cell aggregate in which a RPE65 gene-expressing cell does not appear can be obtained.

To determine such particular period, the aforementioned "cell aggregate comprising a retinal tissue" is used as a sample, and the presence or absence of expression of RPE65 gene contained in the sample or the level thereof may be measured by a general genetic engineering method or a biochemical method. Specifically, for example, the presence or absence of expression of RPE65 gene or the level thereof can be examined by subjecting a cryosection of the aforementioned "cell aggregate comprising a retinal tissue" to an immunostaining method using an antibody against RPE65 protein.

As a "period before the appearance of a RPE65 gene-expressing cell" in step (A), for example, a period during which the ratio of Chx10 positive cells present in the above-mentioned retinal tissue decreases than that at the time of start of the culturing of the aforementioned cell aggregate in a serum-free medium or serum-containing medium each containing a Wnt signal transduction pathway activating substance and/or an FGF signal transduction pathway inhibitor, and falls within the range of 30% to 0% can be mentioned. As the "cell aggregate in which a RPE65 gene-expressing cell does not appear", a cell aggregate in which Chx10 positive cells are present in the above-mentioned retinal tissue in a proportion of within 30% to 0% of the tissue can be mentioned.

While the number of days of the "period before the appearance of a RPE65 gene-expressing cell" in step (A) varies depending on the kind of the Wnt signal transduction pathway activating substance and/or the FGF signal transduction pathway inhibitor, the kind of the serum-free medium or serum-containing medium, other culture conditions and so on, it is, for example, within 14 days. More specifically, when a serum-free medium (e.g., serum-free medium which is a basal medium supplemented with N2) is used, the above-mentioned period is preferably, for example, within 10 days, more preferably, for example, 3 days to 6 days. When a serum-containing medium (e.g., serum-containing medium which is a basal medium supplemented with fetal bovine serum) is used, the aforementioned period is preferably, for example, within 12 days, more preferably, for example, 6 days to 9 days.

Then as step (B), the "cell aggregate in which a RPE65 gene-expressing cell does not appear" obtained by culturing as mentioned above is cultured in a serum-free medium or serum-containing medium each not supplemented with a Wnt signal transduction pathway activating substance.

As a preferable culturing in step (B), suspension culturing can be mentioned.

As the serum-free medium in step (B), a medium which is a basal medium supplemented with N2 or KSR can be mentioned. As the serum-containing medium, a medium which is a basal medium supplemented with fetal bovine serum can be mentioned. More specifically, a serum-containing medium which is a DMEM/F-12 medium supplemented with fetal bovine serum can be mentioned.

The above serum-free medium or serum-containing medium in step (B) may contain a known growth factor, an additive and a chemical substance that promote the growth, and so on. Examples of the known growth factor include EGF, FGF, IGF, insulin and so on. Examples of the additive that promotes the growth include N2 supplement (Life Technologies), B27 supplement (Life Technologies), KSR (Life Technologies) and so on. Examples of the chemical substance that promotes the growth include retinoids (e.g., retinoic acid) and taurine.

A preferable period for the culturing in step (B), for example, a period for the culturing during which the ratio of Chx10 positive cells present in the above- mentioned retinal tissue increases than that at the time of start of the culturing of the aforementioned cell aggregate in a serum-free medium or serum-containing medium each free of a Wnt signal transduction pathway activating substance, and reaches 30% or more can be mentioned.

The culture conditions such as culture temperature, $CO_2$ concentration and the like in step (B) can be appropriately set. The culture temperature is, for example, in the range of about 30° C. to about 40° C., preferably, for example, around about 37° C. The $CO_2$ concentration is, for example, in the range of about 1% to about 10%, preferably, for example, around about 5%.

While the number of the above-mentioned culture days until "a cell aggregate comprising a ciliary marginal zone-like structure" is obtained in step (B) varies depending on the kind of the serum-free medium or serum-containing medium, other culture conditions and so on, it is, for example, within 100 days. The above number of culture days is preferably, for example, 20 days to 70 days, more preferably, for example, 30 days to 60 days.

In a "cell aggregate comprising a ciliary marginal zone-like structure" prepared by the aforementioned step (A) and (B), a retinal pigment epithelium and a retinal tissue (specifically, neural retina) are respectively present adjacent to the ciliary marginal zone-like structure in the same cell aggregate. The structure can be confirmed by microscopic observation and so on. Specifically, for example, the presence of a ciliary marginal zone-like structure as an epithelial structure which is thick in retina side and thin in retinal pigment epithelium side, and which is formed between a retinal tissue having high transparency and retinal pigment epithelium showing pigmentation, can be confirmed by microscopic observation. In addition, the presence of ciliary marginal zone-like structure can be confirmed by identifying Rdh10 positive, Otx1 positive, or Zic1 positive cells with immunostaining of a frozen section of aggregate. A retinal tissue cut out from the obtained ciliary marginal zone-like structure may also be used as a retinal tissue for transplantation.

A retinal pigment epithelial cell can be produced by the following step (C) from a cell aggregate containing a retinal tissue obtained by the production method of the present invention and the like. A retinal pigment epithelial sheet can be produced by the following step (D) from a retinal pigment epithelial cell obtained by the following step (C).

The "retinal pigment epithelial cell" in the present invention means an epithelial cell present on the outside of the neural retinal tissue in retina in vivo. Whether it is a retinal pigment epithelial cell can be confirmed by those of ordinary skill in the art based on, for example, expression of a cell marker (RPE65 (matured retinal pigment epithelial cell), Mitf (juvenile or matured retinal pigment epithelial cell) and the like), the presence of melanin granule, characteristic cell morphology of polygon and the like.

First, in step (C), a cell aggregate containing a retinal tissue obtained by the production method of the present invention is cultured in suspension in a serum-free medium or serum-containing medium not supplemented with a BMP signal pathway activating substance but containing a Wnt signal pathway activating substance to give an aggregate containing retinal pigment epithelial cells.

As a serum-free medium to be used in step (C), a serum-free medium which is a basal medium supplemented with N2 or KSR can be mentioned. More specifically, a serum-free medium which is a DMEM/F-12 medium supplemented with N2 supplement (Life Technologies) can be mentioned. As the serum-containing medium, a serum-containing medium which is a basal medium supplemented with fetal bovine serum can be mentioned.

The serum-free medium to be used in step (C) may contain, in addition to the aforementioned Wnt signal transduction pathway activating substance, the aforementioned Nodal/Activin signal transduction pathway activating substance, and/or the aforementioned FGF signal transduction pathway inhibitor. A preferable culturing in step (C) is, for example, suspension culturing.

Step (D) in which the aggregate obtained in step (C) of the present invention is dispersed and the obtained cells are cultured in an adhered state is explained.

Step (D) is performed within 60 days, preferably within 30 days, more preferably 3 days, after the start of step (C).

As a serum-free medium or serum-containing medium to be used for adhesion culturing in step (D), the aforementioned medium can be mentioned. To avoid complicated preparation, a serum-free medium supplemented with an appropriate amount of a commercially available serum replacement such as KSR and the like (e.g., a medium of 1:1 mixture of DMEM/F-12 and Neurobasal supplemented with 1/2×N2 supplement, 1/2×B27 supplement and 100 μM 2-mercaptoethanol) is preferably used. The amount of KSR to be added to the serum-free medium is, for example, generally about 1% to about 20%, preferably about 2% to about 20%, in the case of a cell derived from human iPS cell.

In step (D), it is preferable to culture cells in the aforementioned serum-free medium or serum-containing medium containing a ROCK inhibitor.

In step (D), it is more preferable to culture cells in a serum-free medium or serum-containing medium further containing one or more substances selected from the group consisting of a Wnt signal pathway activating substance, an FGF signal pathway inhibitor, an Activin signal pathway activating substance and a BMP signal transduction pathway activating substance.

The Activin signal pathway activating substance is a substance capable of enhancing a signal mediated by Activin. Examples of the Activin signal pathway activating substance include proteins belonging to the Activin family (e.g., Activin A, Activin B, Activin C, Activin AB and the like), Activin receptor, and Activin receptor agonist.

The concentration of the Activin signal pathway activating substance to be used in step (D) may be any as long as a uniformed sheet of retinal pigment epithelial cells can be efficiently formed. For example, Recombinant Human/Mouse/Rat Activin A (R&D systems, #338-AC) is added to a concentration of about 1 ng/ml to about 10 μg/ml, preferably about 10 ng/ml to about 1 μg/ml, more preferably about 100 ng/ml.

An Activin signal pathway activating substance is added, for example, within 18 days, preferably on day 6, from the start of step (D).

In step (D), adhesion culturing is preferably performed on a culture vessel whose surface is treated with a culture substrate. As a culture substrate to be used for treating culture vessel in step (D), a cell culture substrate enabling adhesion culturing of aggregate-derived cells and formation of a retinal pigment epithelial sheet can be mentioned.

3. Method for Evaluating Toxicity or Efficacy

Since retinal cells or a retinal tissue containing them produced by the production method of the present invention are useful as a material for a research on disease or drug discovery in a screening for a medicament for treating a disease due to a disorder of a retinal tissue, or in toxicity evaluation, it can be used as a reagent for evaluating toxicity or efficacy of a test substance. For example, iPS cells are produced from a human patient with a disease due to a disorder of a retinal tissue, particularly a hereditary disease, and using the iPS cells, retinal cells or a retinal tissue containing them are produced by the method of the present invention. The retinal cells or the retinal tissue containing them can mimic the disorder of retinal tissue causing the disease of the patient in vitro. Therefore, the present invention provides a method for evaluating toxicity or efficacy of a test substance, which comprises contacting the test substance with retinal cells or a retinal tissue containing them produced by the production method of the present invention, and detecting an effect of the substance on the cells or tissue.

For example, retinal cells or a retinal tissue containing them having a particular disorder (e.g., hereditary disorder), which are produced by the production method of the present invention, are cultured in the presence or absence (negative control) of a test substance. Then, the severity of disorder in the retinal cells or retinal tissue treated with the test substance is compared with that of the negative control. As a result, the test substance that reduced the severity of the disorder can be selected as a candidate substance for a medicament for treating the disease resulting from the disorder. For example, a test substance that improves the physiological activity (e.g., enhanced survival or maturation) of retinal cells or a retinal tissue containing them produced by the production method of the present invention can be screened for a candidate substance of a pharmaceutical product. Alternatively, retinal cells or a retinal tissue containing them are prepared by inducing differentiation of the induced pluripotent stem cells using the production method of the present invention, wherein the induced pluripotent stem cells are prepared from a somatic cell having a gene mutation that causes a particular disorder in a disease accompanied by a disorder in retinal tissue and the like. A candidate test substance effective as a therapeutic drug or prophylactic drug for the disorder can be screened for, based on an index (whether the retinal cells or the retinal tissue containing them added with a test substance show the aforementioned disorder).

For toxicity evaluation, retinal cells or a retinal tissue containing them produced by the production method of the present invention are cultured in the presence or absence (negative control) of a test substance. Then, the severity of toxicity on the retinal cells or a retinal tissue containing them is compared with that of the negative control. As a result, a test substance that exerted toxicity as compared to the negative control can be determined as a substance having toxicity to retinal cells or a retinal tissue containing them.

That is, the present invention encompasses a method for evaluating toxicity comprising the following steps:
(step 1) a step of culturing retinal cells or a retinal tissue containing them produced by the production method of the present invention under viable culture conditions for a given time in the presence of a test substance, and measuring the severity of cell injury,
(step 2) a step of culturing retinal cells or a retinal tissue containing them produced by the production method of the present invention under viable culture conditions for a given time in the absence of test substance or in the presence of a positive control, and measuring the severity of cell injury,
(step 3) a step of evaluating the toxicity of the test substance in step 1, based on the difference in the results measured in (step 1) and (step 2).

As used herein, "in the absence of a test substance" encompasses adding only a culture medium or a solvent used to dissolve the test substance instead of adding a test substance. In addition, "positive control" means a known compound having toxicity.

Examples of the method for measuring the severity of cell injury include a method for measuring the number of viable cells, for example, a method for measuring intracellular ATP amount, a method for measuring the number of viable cells by cell staining (e.g., nucleus staining) and morphology observation and the like.

In step 3, as a method for evaluating the toxicity of a test substance, the measurement value in step 1 and the measurement value of the negative control in step 2 are compared, and when the severity of cell injury in step 1 is high, the test substance can be determined to show toxicity. In addition, the measurement value in step 1 and the measurement value of the positive control in step 2 are compared, and when the severity of cell injury in step 1 is the same or above, the test substance can be determined to show toxicity.

4. Pharmaceutical Composition

The present invention provides a pharmaceutical composition containing an effective amount of retinal cells or a retinal tissue containing them produced by the production method of the present invention.

The pharmaceutical composition containing an effective amount of retinal cells or a retinal tissue containing them produced by the production method of the present invention, and a pharmaceutically acceptable carrier.

As a pharmaceutically acceptable carrier, a physiological aqueous solvent (saline, buffer, serum-free medium etc.) can be used. Where necessary, in a transplantation therapy, a medicament containing a tissue or cells to be transplanted may contain conventionally used preservative, stabilizer, reducing agent, isotonizing agent and the like.

The pharmaceutical composition of the present invention can be produced as a suspension by suspending retinal cells or a retinal tissue containing them produced by the production method in an appropriate physiological aqueous solvent. Where necessary, the composition may be cryopreserved with a cryopreseravative, thawed when in use, washed with buffer, and used for a transplantation therapy.

A retinal tissue obtained by the production method of the present invention may also be cut in an appropriate size with tweezers and the like to give a sheet preparation.

Cells obtained by the production method of the present invention may also be subjected to adhesion culturing in the third step for differentiation induction to form a sheet-like cells to give a sheet preparation.

The pharmaceutical composition of the present invention is useful as a therapeutic drug for a disease due to a disorder of retinal cells or a retinal tissue containing them.

5. Therapeutic Drug and Treatment Method

The retinal cells or a retinal tissue containing them produced by the production method of the present invention are useful for a transplantation therapy for a disease due to (caused by) a disorder thereof. Thus, the present invention provides a therapeutic drug containing retinal cells or a retinal tissue containing them produced by the production method of the present invention for treating a disease due to a disorder of the retinal tissue, and a treatment method comprising administering the therapeutic drug to a patient. The retinal cells or a retinal tissue containing them produced by the production method of the present invention can be used as a medicament for treating a disease due to a disorder of a retinal tissue or to complement the corresponding damaged site in a damaged state of a retinal tissue. A disease due to a disorder of a retinal tissue, and a damaged state of a retinal tissue can be treated by transplanting retinal cells or a retinal tissue containing them produced by the production method of the present invention to a patient with the disease due to the disorder of a retinal tissue, or the damaged state of a retinal tissue, who requires transplantation, to complement the disordered retinal tissue itself. Examples of the disease due to a disorder of a retinal tissue include retinal denaturation, pigmentary degeneration of the retina, age-related macular degeneration, organic mercury poisoning, chloroquine retinopathy, glaucoma, diabetic retinopathy, retinopathy of newborn babies, or the like.

In transplantation therapy, rejection due to the difference in histocompatibility antigens often poses a problem. However, the problem can be solved by using pluripotent stem cells (e.g., induced pluripotent stem cells) established from the somatic cells of the transplantation recipient. That is, in a preferable embodiment, pluripotent stem cells (e.g., induced pluripotent stem cells) established from the somatic cells of the recipient are used as pluripotent stem cells in the method of the present invention, and a neural tissue or neural cells, which is immunologically self for the recipient, are produced and transplanted to the recipient.

In addition, an allogenic retinal tissue or retinal cell may be produced from a pluripotent stem cell (e.g., induced pluripotent stem cell) established from a somatic cell of others who are immunologically compatible with the recipient (e.g., compatible in HLA type and MHC type partly or entirely), and transplanted to the recipient.

EXAMPLES

The present invention is explained in detail in the following by referring to Examples, which are not to be construed as limitative.

Example 1: Production of Retinal Tissue Using Human iPS Cell, Including a Step of Culturing in Medium Containing MEK Inhibitor, and PKC Inhibitor or B-Raf Inhibitor iPS cells derived from human dermal fibroblast established from human dermal fibroblasts (HDF) of Cell Applications, Inc. (201B7 strain, Kyoto University) and iPS cells derived from human peripheral blood derived-mononuclear cells established from ePMBC (registered trade mark) of Cellular Technology Limited (1231A3 strain, Kyoto University) were used. Undifferentiated maintenance culture of these iPS cells under feeder cell-free conditions was performed according to the method described in "Nakagawa, M. et. al., Sci. Rep. 2014 Jan. 8; 4: 3594". As the medium, "StemFit (registered trade mark)" AK03 medium (Ajinomoto Co., Inc.) was used and iMatrix-511 (Nippi) was used as a culture substrate.

Production of retinal tissue including a step of culturing in a medium containing an MEK inhibitor, and a PKC inhibitor or a B-Raf inhibitor was performed as follows. Human iPS cells under culture for maintaining an undifferentiated state were treated with 0.5×TrypLE select (mixture of equal amounts of TrypLE select (Life Technologies) and 0.5 mM EDTA/PBS(−)), scraped using a cell scraper, dispersed to single cells by pipetting, seeded in a 6-well culture plate coated with iMatrix-511 (0.5 μg/cm$^2$) at $1.2\times10^4$ cells per 1 well, and cultured in a StemFit medium containing Y-27632 (Wako Pure Chemical Industries, Ltd.) (final concentration 10 μM) as a ROCK inhibitor under 37° C., 5% $CO_2$ conditions. On the next day of seeding, PD0325901 (SIGMA) (final concentration 1 μM) as an MEK inhibitor and Go6983 (SIGMA) (final concentration 2 μM) as a PKC inhibitor were added and the mixture was cultured for 6 days, or at 2 days after seeding, PD0325901 (final concentration 1 μM) and Go6983 (final concentration 2 μM) were added and the mixture was cultured for 5 days, or at 6 days after seeding, PD0325901 (final concentration 1 μM) and SB-590885 (SIGMA) (final concentration 0.5 μM) as a B-Raf inhibitor were added and the mixture was cultured for 1 day (completion of step 1). The cells cultured in the medium containing the above-mentioned inhibitors were treated with 0.5×TrypLE select, scraped using a cell scraper, dispersed to single cells by pipetting, seeded in a 96-well culture plate (PrimeSurface 96 V-BOTTOM plate, SUMITOMO BAKELITE CO., LTD.) at $1.2\times10^4$ cells per 1 well, and cultured in 100 μl of a gfCDM+KSR medium [45% IMDM (Life Technologies), 45% F12 (Life Technologies), 10% KSR (Life Technologies), 1% Chemically defined lipid concentrate (Life Technologies), 450 μM 1-Thioglycerol (SIGMA)] supplemented with Y-27632 (final concentration 20 μM) and cultured in suspension under 37° C., 5% $CO_2$ conditions. Cell aggregates were formed by day 2 from the start of the suspension culture (i.e., 2 days after the start of the suspension culture) (completion of step 2). On day 3 from the start of the suspension culture (i.e., 3 days after the start of the suspension culture), gfCDM+KSR medium not containing a ROCK inhibitor but containing human recombinant BMP4 (R&D Systems) (4.5 nM) was added by 50 μl per 1 well such that the final concentration of exogeneous human recombinant BMP4 was 1.5 nM (55 ng/ml) (start of step 3). On day 6 (i.e., 6 days after the start of the suspension culture), on day 9 (9 days later), on day 12 (12 days later), on day 15 (15 days later) from the start of the suspension culture, a half amount of the medium was changed to a gfCDM+KSR medium not containing ROCK inhibitor or human recombinant BMP4, on day 18 from the start of suspension culture (18 days after the start of suspension culture), the cell aggregates were transferred to a 90 mm culture dish (petri dish for suspension culture, SUMITOMO BAKELITE CO., LTD.) containing 15 ml of a DMEM/F12+ N2 medium (DMEM/F-12, GlutaMAX (Life Technologies), 1×N2 supplement (Life Technologies), 100 U/ml penicillin-100 μg/ml streptomycin) and continuously cultured in suspension under 37° C., 5% $CO_2$ conditions. On day 20 or 21 from the start of suspension culture (20 or 21 days after the start of suspension culture), the cell aggregates were fixed with 4% para-formaldehyde and cryosections were produced. These cryosections were immunostained for a retinal progenitor cell marker, Chx10 using anti-Chx10 antibody (Exalpha). As a result, Chx10 positive cells were confirmed (FIG. 1).

Example 2: Production of Retinal Tissue Using Human iPS Cell Including a Step of Culturing in Medium Containing MEK Inhibitor±PKC Inhibitor, and a Step of Culturing in Medium Containing Sonic Hedgehog Signal Transduction Pathway Activating Substance iPS cells derived from human peripheral blood derived-mononuclear cells established from ePMBC (registered trade mark) of Cellular Technology Limited (1231A3 strain, Kyoto University) were used. Undifferentiated maintenance culture of these iPS cells under feeder cell-free conditions was performed according to the method described in "Nakagawa, M. et. al., Sci. Rep. 2014 Jan. 8; 4: 3594". As the medium, "StemFit (registered trade mark)" AK03 medium (Ajinomoto Co., Inc.) was used and iMatrix-511 (Nippi) was used as a culture substrate.

Figure 2:
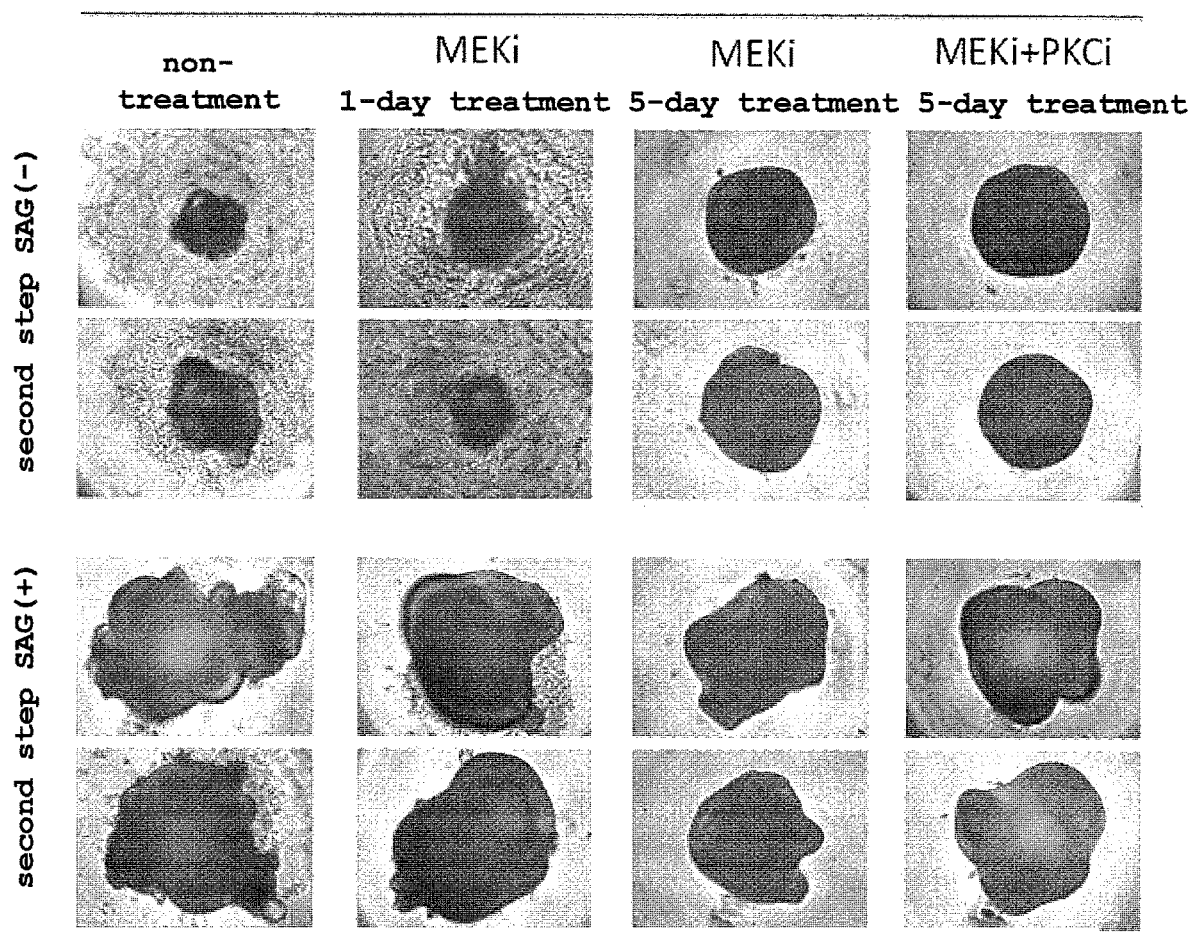
FIG. 2 shows microscopic images of cell aggregates containing retinal progenitor cells derived from human iPS cells produced by a production method of a retinal tissue comprising a step of culturing the human iPS cells in a medium containing an MEK inhibitor, or an MEK inhibitor and a PKC inhibitor, and a step of culturing the obtained cells in a medium containing a Sonic hedgehog signal transduction pathway activating substance. 1231A3: human iPS cells (1231A3 strain) were used. On day 10 after suspension culture. MEKi: MEK inhibitor (1 μM PD0325901), PKCi: PKC inhibitor (2 µM Go6983), SAG: Sonic hedgehog signal transduction pathway activating substance (30 nM SAG).
Figure 3:
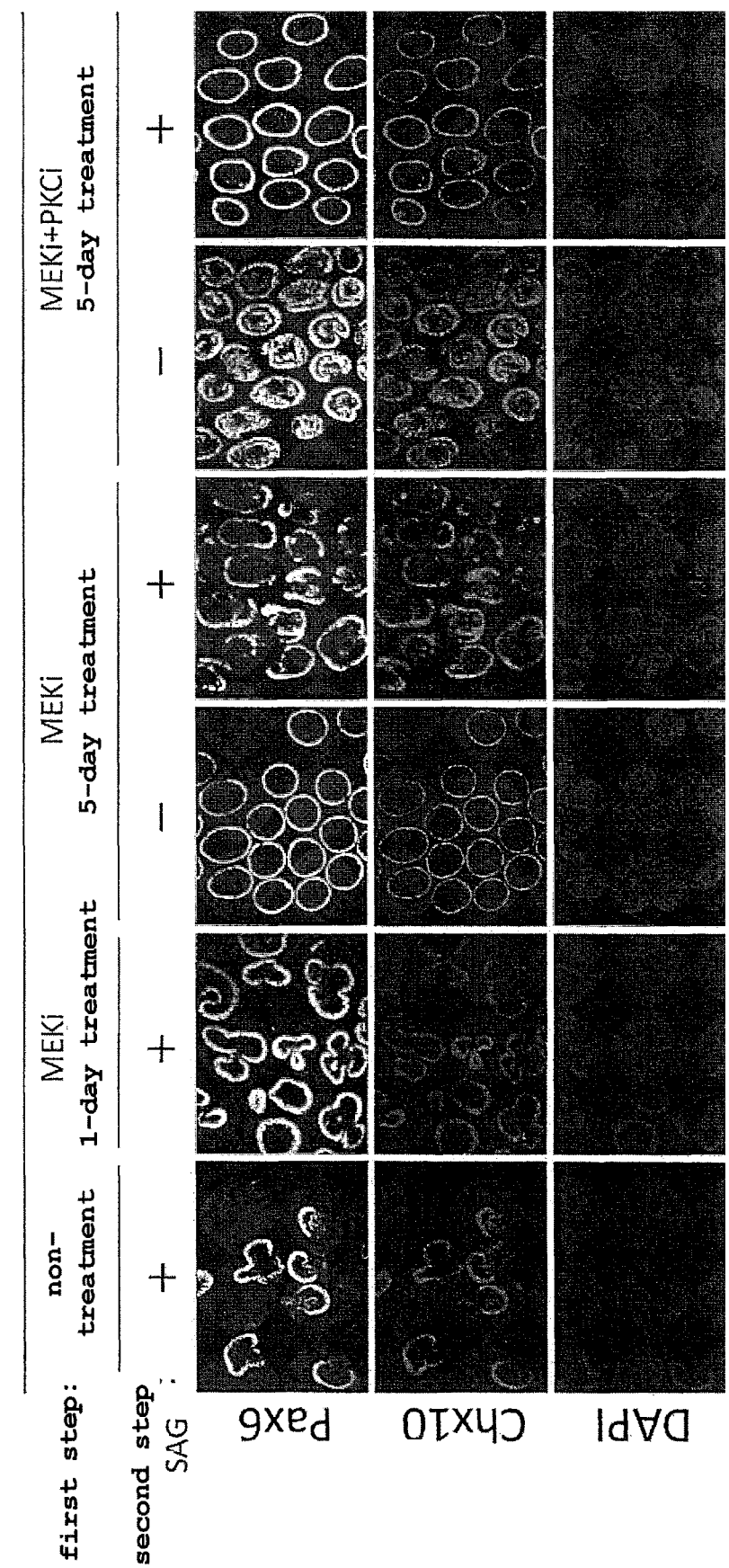
FIG. 3 shows microscopic images of cell aggregates containing retinal progenitor cells derived from human iPS cells produced by a production method of a retinal tissue comprising a step of culturing the human iPS cells in a medium containing an MEK inhibitor±a PKC inhibitor, and a step of culturing the obtained cells in a medium containing a Sonic hedgehog signal transduction pathway activating substance. 1231A3: human iPS cells (1231A3 strain) were used. On day 22 after suspension culture. Pax6: retinal progenitor cell marker. Chx10: retinal progenitor cell marker. DAPI: cell nuclear staining. MEKi: MEK inhibitor (1 µM PD0325901), PKCi: PKC inhibitor (2 µM Go6983), SAG: Sonic hedgehog signal transduction pathway activating substance (30 nM SAG).

Production of retinal tissue including a step of culturing in a medium containing an MEK inhibitor, a PKC inhibitor or a Sonic hedgehog signal transduction pathway activating substance was performed as follows. Human iPS cells under culture for maintaining an undifferentiated state were treated with 0.5×TrypLE select (mixture of equal amounts of TrypLE select (Life Technologies) and 0.5 mM EDTA/PBS (−)), scraped using a cell scraper, dispersed to single cells by pipetting, seeded in a 6-well culture plate coated with iMatrix-511 (0.5 μg/cm$^2$) at $1.2\times10^4$ cells per 1 well, and cultured in a StemFit medium containing Y-27632 (Wako Pure Chemical Industries, Ltd.) (final concentration 10 μM) as a ROCK inhibitor under 37° C., 5% $CO_2$ conditions. At 2 days after the seeding, PD0325901 (SIGMA) (final concentration 1 μM) as an MEK inhibitor and Go6983 (SIGMA) (final concentration 2 μM) as a PKC inhibitor were added and the mixture was cultured for 5 days, or at 6 days after seeding, PD0325901 (final concentration 1 μM) was added and the mixture was cultured for day (completion of step 1). The cells cultured in the medium containing the above-mentioned inhibitors were treated with 0.5×TrypLE select, scraped using a cell scraper, dispersed to single cells by pipetting, seeded in a 96-well culture plate (PrimeSurface 96 V-BOTTOM plate, SUMITOMO BAKELITE CO., LTD.) at $1.0\times10^4$ cells per 1 well, and cultured in 100 μl of a gfCDM+KSR medium [45% IMDM (Life Technologies), 45% F12 (Life Technologies), 10% KSR (Life Technologies), 1% Chemically defined lipid concentrate (Life Technologies), 450 µM 1-Thioglycerol (SIGMA)] supplemented with Y-27632 (final concentration 20 µM) (second step SAG(−)) or seeded in a gfCDM+KSR medium supplemented with SAG (Enzo) (final concentration 30 nM) (second step SAG(+)) and cultured in suspension under 37° C., 5% $CO_2$ conditions. Cell aggregates were formed by 2 days after the start of the suspension culture (completion of step 2). At 3 days after the start of the suspension culture, gfCDM+KSR medium not containing a ROCK inhibitor and SAG but containing human recombinant BMP4 (R&D Systems) (4.5 nM) was added by 50 µl per 1 well such that the final concentration of exogenous human recombinant BMP4 was 1.5 nM (55 ng/ml) (start of step 3). At 6 days, 9 days, 12 days 15 days and 18 days after the start of the suspension culture, a half amount of the medium was changed to a gfCDM+KSR medium not containing ROCK inhibitor, SAG and human recombinant BMP4. At 10 days after the start of the suspension culture, the cell aggregates were observed under a microscope (FIG. 2). As a result, collapse of aggregates was observed in the second step SAG(−) in the non-treatment and 1-day treatment with MEK inhibitor; however, collapse of aggregates was hardly observed in the second step SAG(+). Collapse of aggregates was not observed in the 5-day treatment with MEK inhibitor and the 5-day treatment with MEK inhibitor+PKC inhibitor, irrespective of the presence or absence of SAG in the second step. At 22 days after the start of suspension culture, the cell aggregates were fixed with 4% para-formaldehyde and cryosections were produced. These cryosections were immunostained for retinal progenitor cell markers, Pax6 and Chx10 using anti-Pax6 antibody (Covance) and anti-Chx10 antibody (Exalpha). As a result, Pax6, Chx10 co-positive cells were confirmed (FIG. 3).

INDUSTRIAL APPLICABILITY

According to the production method of the present invention, differentiation of pluripotent stem cells into retinal cells is induced efficiently in the absence of a feeder cell, and a retinal tissue can be produced. The production method of the present invention including use of a retinal tissue is useful in that it can produce a retinal tissue to be a material used in the tests and treatments, for the application to an evaluation of toxicity and efficacy of a pharmaceutical product candidate compound or other chemical substance, or a transplantation material for retinal tissue transplantation treatment.

This application is based on a patent application No. 2015-176897 filed in Japan (filing date: Sep. 8, 2015), the contents of which are incorporated in full herein.

The invention claimed is:

1. A method for producing a retinal cell or a retinal tissue, comprising the following steps:
   (1) a first step of maintaining and/or expanding mammalian pluripotent stem cells comprising culturing the mammalian pluripotent stem cells in the absence of a feeder cell in a medium comprising a factor for maintaining an undifferentiated state, wherein the medium does not contain a mitogen-activated protein kinase kinase (MEK) inhibitor,
   (2) a second step of culturing the mammalian pluripotent stem cells obtained in the first step in the absence of a feeder cell for a period not less than 4 days and not exceeding 30 days in a medium comprising (a) a factor for maintaining an undifferentiated state and (b) a MEK inhibitor, wherein the medium does not contain a transforming growth factor (TGF)-β family signal transduction pathway inhibitor,
   (3) a third step of dispersing cells obtained in the second step and culturing the dispersed cells in suspension to form aggregates, wherein the aggregates are formed within 72 hours after the cells obtained in the second step are dispersed, and wherein six days after the start of the third step, at least 70% of the aggregates are uncollapsed or non-cystic, and
   (4) a fourth step of culturing the aggregates obtained in the third step in suspension in the presence of a bone morphogenetic protein (BMP) signal transduction pathway activating substance in the absence of a basement membrane preparation to obtain aggregates containing a retinal cell or a retinal tissue, wherein the BMP signal transduction pathway activating substance is added to the medium at a point between day 1 and day 9 from the start of the third step.

2. The production method according to claim 1, wherein the medium in the second step further comprises a protein kinase C (PKC) inhibitor or a B-Raf inhibitor.

3. The production method according to claim 2, wherein the PKC inhibitor is Go6983.

4. The production method according to claim 2, wherein the B-Raf inhibitor is SB590885.

5. The production method according to claim 1, wherein the second step is performed under serum-free conditions.

6. The production method according to claim 1, wherein the culture period is 4 days-6 days in the second step.

7. The production method according to claim 1, wherein the second step is performed with an adhesion culture method.

8. The production method according to claim 1, wherein the factor for maintaining an undifferentiated state in the first step and/or the second step is a fibroblast growth factor (FGF) signal transduction pathway activating substance.

9. The production method according to claim 8, wherein the FGF signal transduction pathway activating substance is bFGF.

10. The production method according to claim 1, wherein the MEK inhibitor is PD0325901.

11. The production method according to claim 1, wherein the mammalian pluripotent stem cells are cultured in the presence of a Rho-associated coiled-coil kinase (ROCK) inhibitor in the second step.

12. The production method according to claim 11, wherein the ROCK inhibitor is Y-27632.

13. The production method according to claim 1, wherein the cells are cultured in suspension in a serum-free medium containing a Sonic hedgehog signal transduction pathway activating substance in the third step.

14. The production method according to claim 13, wherein the Sonic hedgehog signal transduction pathway activating substance is Smoothened Agonist (SAG).

15. The production method according to claim 1, wherein, in the third step, the concentration of the Sonic hedgehog signal transduction pathway activating substance in the medium is a concentration corresponding to Sonic hedgehog signal transduction activity of SAG at 10 nM to 700 nM.

16. The production method according to claim 1, wherein the BMP signal transduction pathway activating substance is one or more proteins selected from the group consisting of BMP2, BMP4, BMP7 and Growth Differentiation Factor 7 (GDF7).

17. The production method according to claim 16, wherein the BMP signal transduction pathway activating substance is BMP4.

18. The production method according to claim 13, wherein, in the fourth step, the BMP signal transduction pathway activating substance is added to the medium at a point between day 3 and day 6 from the start of the third step.

19. The production method according to claim 1, wherein the pluripotent stem cell is an induced pluripotent stem cell.

20. The production method according to claim 19, wherein the induced pluripotent stem cell is a human induced pluripotent stem cell.

21. The production method according to claim 1, wherein the medium in the second step does not further contain a Sonic hedgehog signal transduction pathway activating substance.

22. The production method according to claim 1, wherein, in the fourth step, the aggregates are cultured in suspension in the presence of a BMP signal transduction pathway activating substance until a cell expressing a Rx gene, Pax6 gene, and/or Chx10 gene appears.

23. The production method according to claim 1, wherein the cells obtained in the second step contain cells maintaining pluripotent-like properties.

24. A method for producing a retinal tissue comprising:
   (1) producing cell aggregates comprising a retinal tissue by the production method according to claims 1, and
   (2) cutting out the retinal tissue from the cell aggregates.

* * * * *